(12) United States Patent
Chiou et al.

(10) Patent No.: US 8,962,587 B2
(45) Date of Patent: Feb. 24, 2015

(54) GENE DELIVERY OF OCT4 AND SIRT1 AND PHARMACEUTICAL COMPOSITIONS THEREOF

(75) Inventors: Shih-Hwa Chiou, Taipei (TW); Jong-Yuh Cherng, Chiayi County (TW)

(73) Assignee: Taipei Veterans General Hospital, Taipei (TW)

( * ) Notice: Subject to any disclaimer, the term of this patent is extended or adjusted under 35 U.S.C. 154(b) by 167 days.

(21) Appl. No.: 13/600,842

(22) Filed: Aug. 31, 2012

(65) Prior Publication Data
US 2013/0052238 A1 Feb. 28, 2013

Related U.S. Application Data

(60) Provisional application No. 61/529,455, filed on Aug. 31, 2011.

(51) Int. Cl.
*C12N 15/63* (2006.01)
*C12N 15/87* (2006.01)
*A61K 31/711* (2006.01)
*C07K 14/47* (2006.01)
*A61K 48/00* (2006.01)

(52) U.S. Cl.
CPC .............. *C12N 15/87* (2013.01); *A61K 31/711* (2013.01); *C07K 14/4702* (2013.01); *A61K 48/005* (2013.01)
USPC ........................ 514/44 R; 435/455; 435/320.1

(58) Field of Classification Search
CPC ..... A61K 35/30; A61K 48/00; C12N 5/0696; C12N 5/0606; C12N 2501/603; C12N 2510/00; C12N 5/0695; C12N 15/63; C12N 2501/60; C12N 2506/00; C12N 15/87; C12N 2320/30; C12N 2320/32; C12N 2330/10; C12N 2506/45; C12N 5/0692
USPC ................... 435/455, 6.1, 325; 424/93.7, 400
See application file for complete search history.

(56) References Cited

FOREIGN PATENT DOCUMENTS

WO      WO 0231111 A2 *    4/2002
WO      WO 2009061442 A1 *  5/2009  ............. C12N 15/00

OTHER PUBLICATIONS

Kim et al, Cell, 2009, 136:411-419.*
Vaziri et al, Cell, 2001, 107:149-159.*
Dolgin, Nature Reports Stem Cells, Published online: Aug. 20, 2009 | doi:10.1038/stemcells.2009.112.*
Parker et al, Stem Cells and Development, 2009, 18:803-806.*
Liu et al, Biomaterials, 2009, 30:6665-6673.*

* cited by examiner

*Primary Examiner* — Peter Paras, Jr.
*Assistant Examiner* — Chi-Feng Hsu
(74) *Attorney, Agent, or Firm* — WPAT, P.C.; Anthony King; Kay Yang

(57) ABSTRACT

The present invention provides a method for decreasing the level of methylation of Oct4 promoter in a target cell, comprising transfecting the target cell with the combination of Oct4 cDNA and SirT1 cDNA. The invention also provides a method for inducing cytoprotective responses of a target cell, comprising transfecting the target cell with the combination of Oct4 cDNA and SirT1 cDNA. The invention further provides a pharmaceutical composition comprising Oct4 cDNA and SirT1 cDNA, or a polynucleotide comprising Oct4 cDNA and SirT1 cDNA.

8 Claims, 18 Drawing Sheets

A

B

SEQUENCE LISTING

```
<160> NUMBER OF SEQ ID NOS: 36

<210> SEQ ID NO 1
<211> LENGTH: 1410
<212> TYPE: DNA
<213> ORGANISM: Homo sapiens

<400> SEQUENCE: 1
cttcgcaagc cctcatttca ccaggccccc ggcttggggc gccttccttc cccatggcgg      60
gacacctggc ttcggatttc gccttctcgc ccctccagg tggtggaggt gatgggccag     120
gggggccgga gccgggctgg gttgatcctc ggacctggct aagcttccaa ggccctcctg     180
gagggccagg aatcgggccg ggggttgggc caggctctga ggtgtggggg attccccat     240 gccccccgcc gtatgagttc tgtgggggga tggcgtactg tgggcccag gttggagtgg     300
```

```
ggctagtgcc ccaaggcggc ttggagacct ctcagcctga gggcgaagca ggagtcgggg      360
tggagagcaa ctccgatggg gcctccccgg agccctgcac cgtcacccct ggtgccgtga      420
agctggagaa ggagaagctg gagcaaaacc cggaggagtc ccaggacatc aaagctctgc      480
agaaagaact cgagcaattt gccaagctcc tgaagcagaa gaggatcacc ctgggatata      540
cacaggccga tgtggggctc accctggggg ttctatttgg gaaggtattc agccaaacga      600
ccatctgccg ctttgaggct ctgcagctta gcttcaagaa catgtgtaag ctgcggccct      660
tgctgcagaa gtgggtggag gaagctgaca acaatgaaaa tcttcaggag atatgcaaag      720
cagaaaccct cgtgcaggcc cgaaagagaa agcgaaccag tatcgagaac cgagtgagag      780
gcaacctgga gaatttgttc ctgcagtgcc cgaaacccac actgcagcag atcagccaca      840
tcgcccagca gcttgggctc gagaaggatg tggtccgagt gtggttctgt aaccggcgcc      900
agaagggcaa gcgatcaagc agcgactatg cacaacgaga ggattttgag gctgctgggt      960
ctcctttctc agggggacca gtgtcctttc ctctggcccc agggcccat tttggtaccc     1020 caggctatgg gagccctcac ttcactgcac tgtactcctc ggtcccttc cctgagggg     1080 aagcctttcc ccctgtctcc gtcaccactc tgggctctcc catgcattca aactgaggtg     1140
cctgcccttc taggaatggg ggacagggg agggggaggag ctagggaaag aaaacctgga     1200
gtttgtgcca gggttttttgg gattaagttc ttcattcact aaggaaggaa ttgggaacac     1260
aaagggtggg ggcaggggag tttggggcaa ctggttggag ggaaggtgaa gttcaatgat     1320
gctcttgatt ttaatcccac atcatgtatc acttttttct taaataaaga agcctgggac     1380
acagtagata gacacactta aaaaaaaaaa                                      1410

<210> SEQ ID NO 2
<211> LENGTH: 4110
<212> TYPE: DNA
<213> ORGANISM: Homo sapiens

<400> SEQUENCE: 2
gtcgagcggg agcagaggag gcgagggagg agggccagag aggcagttgg aagatggcgg       60
acgaggcggc cctcgcccctt cagcccggcg gctcccccte ggcggcgggg gccgacaggg      120
aggccgcgtc gtcccccgcc ggggagccgc tccgcaagag gccgcggaga gatggtcccg      180
gcctcgagcg gagcccgggc gagcccggtg gggcggcccc agagcgtgag gtgccggcgg      240
cggccagggg ctgcccgggt gcggcggcgg cggcgctgtg gcgggaggcg gaggcagagg      300
cggcggcggc aggcggggag caagaggccc aggcgactgc ggcggctggg gaaggagaca      360
atgggccggg cctgcagggc ccatctcggg agccaccgct ggccgacaac ttgtacgacg      420
aagacgacga cgacgagggc gaggaggagg aagaggcggc ggcggcggcg attgggtacc      480
gagataacct tctgttcggt gatgaaatta tcactaatgg ttttcattcc tgtgaaagtg      540
atgaggagga tagagcctca catgcaagct ctagtgactg gactccaagg ccacggatag      600
gtccatatac ttttgttcag caacatctta tgattggcac agatcctcga acaattctta      660
aagatttatt gccggaaaca ataccctccac ctgagttgga tgatatgaca ctgtggcaga      720
ttgttattaa tatcctttca gaaccaccaa aaggaaaaa agaaaagat attaatacaa      780 ttgaagatgc tgtgaaatta ctgcaagagt gcaaaaaat tatagttcta actggagctg      840
gggtgtctgt ttcatgtgga ataccctgact tcaggtcaag ggatggtatt tatgctcgcc      900
ttgctgtaga cttcccagat cttccagatc ctcaagcgat gtttgatatt gaatatttca      960
```

```
gaaaagatcc aagaccattc ttcaagtttg caaaggaaat atatcctgga caattccagc    1020
catctctctg tcacaaattc atagccttgt cagataagga aggaaaacta cttcgcaact    1080
atacccagaa catagacacg ctggaacagg ttgcgggaat ccaaaggata attcagtgtc    1140
atggttcctt tgcaacagca tcttgcctga tttgtaaata caaagttgac tgtgaagctg    1200
tacgaggaga tatttttaat caggtagttc ctcgatgtcc taggtgccca gctgatgaac    1260
cgcttgctat catgaaacca gagattgtgt ttttggtga aaatttacca gaacagtttc    1320
atagagccat gaagtatgac aaagatgaag ttgacctcct cattgttatt gggtcttccc    1380
tcaaagtaag accagtagca ctaattccaa gttccatacc ccatgaagtg cctcagatat    1440
taattaatag agaacctttg cctcatctgc attttgatgt agagcttctt ggagactgtg    1500
atgtcataat taatgaattg tgtcataggt taggtggtga atatgccaaa ctttgctgta    1560
accctgtaaa gctttcagaa attactgaaa aacctccacg aacacaaaaa gaattggctt    1620
atttgtcaga gttgccaccc acacctcttc atgtttcaga agactcaagt tcaccagaaa    1680
gaacttcacc accagattct tcagtgattg tcacactttt agaccaagca gctaagagta    1740
atgatgattt agatgtgtct gaatcaaaag gttgtatgga agaaaaacca caggaagtac    1800
aaacttctag gaatgttgaa agtattgctg aacagatgga aaatccggat ttgaagaatg    1860
ttggttctag tactggggag aaaaatgaaa gaacttcagt ggctggaaca gtgagaaaat    1920
gctggcctaa tagagtggca aaggagcaga ttagtaggcg gcttgatggt aatcagtatc    1980 tgttttgcc accaaatcgt tacattttcc atggcgctga ggtatattca gactctgaag    2040
atgacgtctt atcctctagt tcttgtggca gtaacagtga tagtgggaca tgccagagtc    2100
caagtttaga agaacccatg gaggatgaaa gtgaaattga agaattctac aatggcttag    2160
aagatgagcc tgatgttcca gagagagctg gaggagctgg attgggact gatggagatg    2220 atcaagaggc aattaatgaa gctatatctg tgaaacagga agtaacagac atgaactatc    2280
catcaaacaa atcatagtgt aataattgtg caggtacagg aattgttcca ccagcattag    2340
gaactttagc atgtcaaaat gaatgtttac ttgtgaactc gatagagcaa ggaaaccaga    2400
aaggtgtaat atttataggt tggtaaaata gattgttttt catggataat tttaacttc     2460 attatttctg tacttgtaca aactcaacac taacttttt ttttttaaaa aaaaaaggt      2520 actaagtatc ttcaatcagc tgttggtcaa gactaacttt cttttaaagg ttcatttgta    2580
tgataaattc atatgtgtat atataatttt ttttgttttg tctagtgagt ttcaacattt    2640
ttaaagtttt caaaaagcca tcggaatgtt aaattaatgt aaagggaaca gctaatctag    2700
accaaagaat ggtattttca ctttctttg taacattgaa tggtttgaag tactcaaaat     2760
ctgttacgct aaacttttga ttctttaaca caattatttt taaacactgg cattttccaa    2820
aactgtggca gctaactttt taaaatctca aatgacatgc agtgtgagta aaggaagtc     2880 aacaatatgt ggggagagca ctcggttgtc tttacttta aaagtaatac ttggtgctaa     2940
gaatttcagg attattgtat ttacgttcaa atgaagatgg cttttgtact tcctgtggac    3000
atgtagtaat gtctatattg gctcataaaa ctaacctgaa aaacaaataa atgctttgga    3060
aatgtttcag ttgcttttaga aacattagtg cctgcctgga tccccttagt tttgaaatat   3120
ttgccattgt tgtttaaata cctatcactg tggtagagct tgcattgatc ttttccacaa    3180
gtattaaact gccaaaatgt gaatatgcaa agcctttctg aatctataat aatggtactt    3240
ctactgggga gagtgtaata ttttggactg ctgttttcca ttaatgagga gagcaacagg    3300
cccctgatta tacagttcca aagtaataag atgttaattg taattcagcc agaaagtaca    3360
```

```
tgtctcccat tgggaggatt tggtgttaaa taccaaactg ctagccctag tattatggag    3420
atgaacatga tgatgtaact tgtaatagca gaatagttaa tgaatgaaac tagttcttat    3480
aatttatctt tatttaaaag cttagcctgc cttaaaacta gagatcaact ttctcagctg    3540
caaaagcttc tagtctttca agaagttcat actttatgaa attgcacagt aagcatttat    3600
ttttcagacc attttttgaac atcactccta aattaataaa gtattcctct gttgctttag    3660
tatttattac aataaaaagg gtttgaaata tagctgttct ttatgcataa aacacccagc    3720
taggaccatt actgccagag aaaaaaatcg tattgaatgg ccatttccct acttataaga    3780
tgtctcaatc tgaatttatt tggctacact aaagaatgca gtatatttag ttttccattt    3840
gcatgatgtt tgtgtgctat agatgatatt ttaaattgaa aagtttgttt taaattattt    3900
ttacagtgaa gactgttttc agctcttttt atattgtaca tagtctttta tgtaatttac    3960
tggcatatgt tttgtagact gtttaatgac tggatatctt ccttcaactt ttgaaataca    4020
aaaccagtgt ttttttacttg tacactgttt taaagtctat taaaattgtc atttgactttt    4080 tttctgttaa cttaaaaaaa aaaaaaaaaa                                    4110
```

```
<210> SEQ ID NO 3
<211> LENGTH: 19
<212> TYPE: DNA
<213> ORGANISM: Artificial Sequence
<220> FEATURE:
<223> OTHER INFORMATION: Primer-F

<400> SEQUENCE: 3
gtggagagca actccgatg                                                 19

<210> SEQ ID NO 4
<211> LENGTH: 20
<212> TYPE: DNA
<213> ORGANISM: Artificial Sequence
<220> FEATURE:
<223> OTHER INFORMATION: Primer-R

<400> SEQUENCE: 4
tgctccagct tctccttctc                                                20

<210> SEQ ID NO 5
<211> LENGTH: 23
<212> TYPE: DNA
<213> ORGANISM: Artificial Sequence
<220> FEATURE:
<223> OTHER INFORMATION: Primer-F

<400> SEQUENCE: 5
cgtcttatcc tctagttctt gtg                                            23

<210> SEQ ID NO 6
<211> LENGTH: 21
<212> TYPE: DNA
<213> ORGANISM: Artificial Sequence
<220> FEATURE:
<223> OTHER INFORMATION: Primer-R

<400> SEQUENCE: 6
atctccatca gtcccaaatc c                                              21

<210> SEQ ID NO 7
<211> LENGTH: 24
<212> TYPE: DNA
```

-continued

<213> ORGANISM: Artificial Sequence
<220> FEATURE:
<223> OTHER INFORMATION: Primer-F

<400> SEQUENCE: 7
gacaggggga ggggaggagc tagg                                             24

<210> SEQ ID NO 8
<211> LENGTH: 26
<212> TYPE: DNA
<213> ORGANISM: Artificial Sequence
<220> FEATURE:
<223> OTHER INFORMATION: Primer-R

<400> SEQUENCE: 8
cttccctcca accagttgcc ccaaac                                           26

<210> SEQ ID NO 9
<211> LENGTH: 23
<212> TYPE: DNA
<213> ORGANISM: Artificial Sequence
<220> FEATURE:
<223> OTHER INFORMATION: Primer-F

<400> SEQUENCE: 9
attcaggaca gccctgattc ttc                                              23

<210> SEQ ID NO 10
<211> LENGTH: 22
<212> TYPE: DNA
<213> ORGANISM: Artificial Sequence
<220> FEATURE:
<223> OTHER INFORMATION: Primer-R

<400> SEQUENCE: 10
tttttgcgac actcttctct gc                                               22

<210> SEQ ID NO 11
<211> LENGTH: 21
<212> TYPE: DNA
<213> ORGANISM: Artificial Sequence
<220> FEATURE:
<223> OTHER INFORMATION: Primer-F

<400> SEQUENCE: 11
aggaccgcca cccacacttg t                                                21

<210> SEQ ID NO 12
<211> LENGTH: 22
<212> TYPE: DNA
<213> ORGANISM: Artificial Sequence
<220> FEATURE:
<223> OTHER INFORMATION: Primer-R

<400> SEQUENCE: 12
ggtcagttca tctgagcggg cg                                               22

<210> SEQ ID NO 13
<211> LENGTH: 21
<212> TYPE: DNA
<213> ORGANISM: Artificial Sequence
<220> FEATURE:
<223> OTHER INFORMATION: Primer-F

<400> SEQUENCE: 13
cgagtggaaa cttttgtcgg a                                                21

<210> SEQ ID NO 14
<211> LENGTH: 16
<212> TYPE: DNA
<213> ORGANISM: Artificial Sequence
<220> FEATURE:
<223> OTHER INFORMATION: Primer-R

<400> SEQUENCE: 14
tgtgcagcgc tcgcag                                                    16

<210> SEQ ID NO 15
<211> LENGTH: 25
<212> TYPE: DNA
<213> ORGANISM: Artificial Sequence
<220> FEATURE:
<223> OTHER INFORMATION: Primer-F

<400> SEQUENCE: 15
tcacacaaca acacaaatgg ctggt                                          25

<210> SEQ ID NO 16
<211> LENGTH: 23
<212> TYPE: DNA
<213> ORGANISM: Artificial Sequence
<220> FEATURE:
<223> OTHER INFORMATION: Primer-R

<400> SEQUENCE: 16
gcccgtggtg tggttgaaat ggt                                            23

<210> SEQ ID NO 17
<211> LENGTH: 25
<212> TYPE: DNA
<213> ORGANISM: Artificial Sequence
<220> FEATURE:
<223> OTHER INFORMATION: Primer-F

<400> SEQUENCE: 17
cgtgattttt tactacctgg gctta                                          25

<210> SEQ ID NO 18
<211> LENGTH: 16
<212> TYPE: DNA
<213> ORGANISM: Artificial Sequence
<220> FEATURE:
<223> OTHER INFORMATION: Primer-R

<400> SEQUENCE: 18
agcctcgggt ggtcgg                                                    16

<210> SEQ ID NO 19
<211> LENGTH: 20
<212> TYPE: DNA
<213> ORGANISM: Artificial Sequence
<220> FEATURE:
<223> OTHER INFORMATION: Primer-F

<400> SEQUENCE: 19
gggccgaaca gacacagccc                                                20

<210> SEQ ID NO 20
<211> LENGTH: 20
<212> TYPE: DNA
<213> ORGANISM: Artificial Sequence
<220> FEATURE:

<223> OTHER INFORMATION: Primer-R

<400> SEQUENCE: 20
gctggggact gggggttgca                                                    20

<210> SEQ ID NO 21
<211> LENGTH: 21
<212> TYPE: DNA
<213> ORGANISM: Artificial Sequence
<220> FEATURE:
<223> OTHER INFORMATION: Primer-F

<400> SEQUENCE: 21
agatcgccct acagccgtcg g                                                  21

<210> SEQ ID NO 22
<211> LENGTH: 21
<212> TYPE: DNA
<213> ORGANISM: Artificial Sequence
<220> FEATURE:
<223> OTHER INFORMATION: Primer-R

<400> SEQUENCE: 22
acggcgctct tcaattgcct t                                                  21

<210> SEQ ID NO 23
<211> LENGTH: 21
<212> TYPE: DNA
<213> ORGANISM: Artificial Sequence
<220> FEATURE:
<223> OTHER INFORMATION: Primer-F

<400> SEQUENCE: 23
tatggcgacg aaggccgtgt g                                                  21

<210> SEQ ID NO 24
<211> LENGTH: 22
<212> TYPE: DNA
<213> ORGANISM: Artificial Sequence
<220> FEATURE:
<223> OTHER INFORMATION: Primer-R

<400> SEQUENCE: 24
tgaggacctg cactggtaca gc                                                 22

<210> SEQ ID NO 25
<211> LENGTH: 20
<212> TYPE: DNA
<213> ORGANISM: Artificial Sequence
<220> FEATURE:
<223> OTHER INFORMATION: Primer-F

<400> SEQUENCE: 25
ccacgcggcc tacgtgaaca                                                    20

<210> SEQ ID NO 26
<211> LENGTH: 20
<212> TYPE: DNA
<213> ORGANISM: Artificial Sequence
<220> FEATURE:
<223> OTHER INFORMATION: Primer-R

<400> SEQUENCE: 26
tggcttccag caactcccct                                                    20

<210> SEQ ID NO 27
<211> LENGTH: 21
<212> TYPE: DNA
<213> ORGANISM: Artificial Sequence
<220> FEATURE:
<223> OTHER INFORMATION: Primer-F

<400> SEQUENCE: 27
gcttcagggc cgccttttg c                                              21

<210> SEQ ID NO 28
<211> LENGTH: 20
<212> TYPE: DNA
<213> ORGANISM: Artificial Sequence
<220> FEATURE:
<223> OTHER INFORMATION: Primer-R

<400> SEQUENCE: 28
atgcacatcg ggccgtcacg                                               20

<210> SEQ ID NO 29
<211> LENGTH: 22
<212> TYPE: DNA
<213> ORGANISM: Artificial Sequence
<220> FEATURE:
<223> OTHER INFORMATION: Primer-F

<400> SEQUENCE: 29
tttgggcatc aggagaacgc ca                                            22

<210> SEQ ID NO 30
<211> LENGTH: 20
<212> TYPE: DNA
<213> ORGANISM: Artificial Sequence
<220> FEATURE:
<223> OTHER INFORMATION: Primer-R

<400> SEQUENCE: 30
gggtcggtca taagcgcggt                                               20

<210> SEQ ID NO 31
<211> LENGTH: 20
<212> TYPE: DNA
<213> ORGANISM: Artificial Sequence
<220> FEATURE:
<223> OTHER INFORMATION: Primer-F

<400> SEQUENCE: 31
aattgagccc gcagcctccc                                               20

<210> SEQ ID NO 32
<211> LENGTH: 20
<212> TYPE: DNA
<213> ORGANISM: Artificial Sequence
<220> FEATURE:
<223> OTHER INFORMATION: Primer-R

<400> SEQUENCE: 32
ccaggcgccc aatacgacca                                               20

<210> SEQ ID NO 33
<211> LENGTH: 22
<212> TYPE: DNA
<213> ORGANISM: Artificial Sequence
<220> FEATURE:
<223> OTHER INFORMATION: Primer-F

```
<400> SEQUENCE: 33
cgggagtctg aaagggccaa gc                                              22

<210> SEQ ID NO 34
<211> LENGTH: 22
<212> TYPE: DNA
<213> ORGANISM: Artificial Sequence
<220> FEATURE:
<223> OTHER INFORMATION: Primer-R

<400> SEQUENCE: 34
gtccgcgttg tgtcaggtct ga                                              22

<210> SEQ ID NO 35
<211> LENGTH: 22
<212> TYPE: DNA
<213> ORGANISM: Artificial Sequence
<220> FEATURE:
<223> OTHER INFORMATION: Primer-F

<400> SEQUENCE: 35
gggctctctg ctcctccctg tt                                              22

<210> SEQ ID NO 36
<211> LENGTH: 20
<212> TYPE: DNA
<213> ORGANISM: Artificial Sequence
<220> FEATURE:
<223> OTHER INFORMATION: Primer-R

<400> SEQUENCE: 36
aggcgtccga tacggccaaa                                                 20
```

US 8,962,587 B2

GENE DELIVERY OF OCT4 AND SIRT1 AND PHARMACEUTICAL COMPOSITIONS THEREOF

This application claim benefit under 35 U.S.C 119(e) of U.S. Provisional Application No. 61/529,455, filed Aug. 31, 2011, the entire content of which is incorporated by reference herein.

FIELD OF THE INVENTION

The present invention relates to epigenetic modification of genomic DNA in mammalian (including human) cells. In particular, the present invention relates to methods and compositions for decreasing the level of methylation of Oct4 promoter in mammalian (including human) cells.

BACKGROUND OF THE INVENTION

Oct4, a member of the POU-domain transcription factor family, is expressed in pluripotent embryonic stem and germ cells (Okamoto et al., Cell. (1990), 60(3):461-72; Rosner et al., Nature (1990), 345(6277):686-92; and Burdon et al., Trends Cell Biol. (2002), 12(9):432-8). The expression of Oct4 is downregulated during differentiation, suggesting that Oct4 plays a pivotal role in mammalian development (Pesce et al., Mech Dev. 1998; 71(1-2):89-98). SirT1 is necessary for the maintenance of genomic stability, which renders it a potential target for eukaryotic anti-aging research (Oberdoerffer et al., Cell. 2008; 135(5):907-18). The SirT1-related life-extension effect and its neuroprotective capacity have been attributed to its ability to enhance the antioxidative stress response and reduce inflammatory damage (Sedding et al., Biol. Chem. 2008; 389(3):279-83; and Gan et al., Aging Cell. 2010; 9(5):924-9).

Cellular reprogramming has the ability to counteract the mechanisms of cellular aging and bring the cells to a self-renewing, rejuvenescent state (Prigione et al., Stem Cells. 2010; 28(4):721-33; and Li et al., Biomaterials. 2011; 32(26): 5994-6005). A low degree of DNA methylation in the promoter region of pluripotency regulators, such as Oct4, is representative of stem cells or reprogramming pluripotent stem cells (Okita et al., Nature. 2007; 448(7151):313-7; and Mikkelsen et al., Nature. 2008; 454(7200):49-55). Self-renewal and pluripotency are important features of embryonic stem cells, and Oct4 plays a key role in the maintenance of these processes (Burdon et al., Trends Cell Biol. 2002; 12(9): 432-8; and Boiani et al., Nat Rev Mol Cell Biol. 2005; 6(11): 872-84). Endogenous Oct4 expression is essential for maintaining stem-like pluripotency (Boiani et al., Genes Dev. 2002; 16(10):1209-19), and demethylation of the Oct4 promoter has been considered a potent hallmark of the nuclear reprogramming process (Lowry et al., Proc Natl Acad Sci USA. 2008; 105(8):2883-8).

BRIEF SUMMARY OF THE INVENTION

The present invention is based on the unexpected finding that exogenous expression of the combination of Oct4 and SirT1 in a target cell induced endogenous Oct4 transcription via decreasing the level of methylation of Oct4 promoter of the cell. Accordingly, the present invention provides methods and compositions for decreasing the level of methylation of Oct4 promoter in a target cell and rejuvenating the target cell.

In one aspect, the present invention provides a method for decreasing the level of methylation of Oct4 promoter in a target cell, comprising transfecting the target cell with the combination of a DNA fragment coding for Oct4 (called as "Oct4 cDNA") and a DNA fragment coding for SirT1 (called as "SirT1 cDNA) whereby the level of methylation of Oct4 promoter in said target cell is decreased.

In another aspect, the invention provides a method for inducing endogenous Oct4 transcription in a target cell, comprising transfecting the target cell with the combination of Oct4 cDNA and SirT1 cDNA in an amount effective to induce endogenous Oct4 transcription in said target cell.

Also provided is a method for inducing cytoprotective responses of a target cell, comprising transfecting the target cell with the combination of Oct4 cDNA and SirT1 cDNA in an amount effective to decrease the level of methylation of Oct4 promoter in said target cell whereby the cytoprotective responses of said target cell is induced.

Further provided is a pharmaceutical composition comprising Oct4 cDNA and SirT1 cDNA, or a polynucleotide comprising Oct4 cDNA and SirT1 cDNA.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Figure 1:
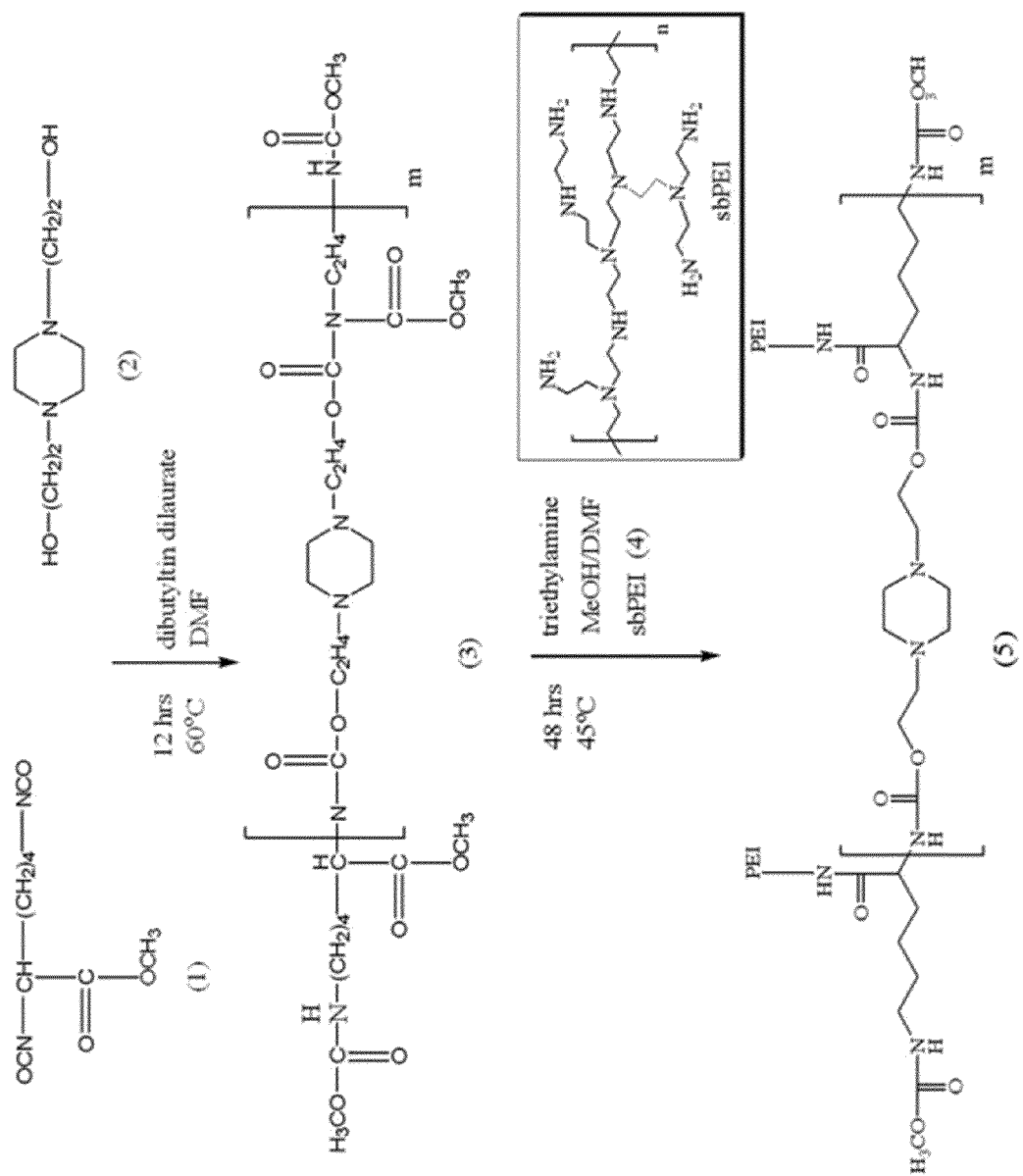
FIG. 1 illustrates the synthesis of polyurethane and PU-short branch polyethylenimine (PU-PEI, also abbreviated as PU).

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

In one aspect, the present invention provides a method for decreasing the level of methylation of Oct4 promoter in a target cell, comprising transfecting the target cell with the combination of a DNA fragment coding for Oct4 (called as "Oct4 cDNA") and a DNA fragment coding for SirT1 (called as "SirT1 cDNA) whereby the level of methylation of Oct4 promoter in said target cell is decreased.

As used herein, the term "promoter" refers to a region within a gene to which transcription factors and/or RNA polymerase can bind so as to control expression of an associated coding sequence. Promoters are commonly, but not always, located in the 5' non-coding regions of genes, upstream of the translation initiation codon.

In another aspect, the present invention provides a method for inducing endogenous Oct4 transcription in a target cell, comprising transfecting the target cell with the combination of Oct4 cDNA and SirT1 cDNA in an amount effective to induce endogenous Oct4 transcription in said target cell.

As used herein, "endogenous" refers to a material that is naturally produced by the genome of the cell.

The term "transcription" as used herein refers to the synthesis of RNA by RNA polymerase, following a DNA template. Transcription is the first step of gene expression and the most important step for the regulation of gene expression.

On the other hand, the present invention provides a method for inducing cytoprotective responses of a target cell, comprising transfecting the target cell with the combination of Oct4 cDNA and SirT1 cDNA in an amount effective to decrease the level of methylation of Oct4 promoter in said target cell whereby the cytoprotective responses of said target cell is induced.

As used herein, "cytoprotective responses" refers to cellular mechanisms that provide protection to cells against harmful agents. Cytoprotective responses include but are not limited to upregulation of antioxidative activity.

In one embodiment of the invention, the transfection is effected by introducing to the target cell the combination of Oct4 cDNA and SirT1 cDNA. In one example, the Oct4 cDNA and SirT1 cDNA may be carried by vectors.

In one embodiment, the Oct4 cDNA comprises the nucleic acid sequence of SEQ ID NO: 1. In another embodiment, the SirT1 cDNA comprises the nucleic acid sequence of SEQ ID NO: 2.

In one embodiment of the invention, the vector is delivered by a polymer.

In a certain example, the polymer is cationic polyurethane-short branch polyethylenimine (PU-sbPEI).

In some embodiments of the invention, the Oct4 cDNA and the SirT1 cDNA are in a ratio of between 0.5:1 and 2:1, preferably 0.8:1-1.2:1. In a certain example, the Oct4 cDNA and the SirT1 cDNA are in a ratio of 1:1.

The present invention also provides a pharmaceutical composition comprising Oct4 cDNA and SirT1 cDNA, or a polynucleotide comprising Oct4 cDNA and SirT1 cDNA. In some embodiments, the Oct4 cDNA, SirT1 cDNA or the polynucleotide comprising both cDNAs is carried by a vector. In examples of the present invention, the vector carrying Oct4 cDNA, SirT1 cDNA, or a polynucleotide comprising both cDNAs is encapsulated in a polymer.

The present invention is further illustrated by the following examples, which are provided for the purpose of demonstration rather than limitation.

EXAMPLES

1. Materials and Methods 1.1 Isolation of Human AMD and Non-AMD Retinas

This research followed the tenets of the Declaration of Helsinki, and informed consent was obtained from the donor patients, whose characteristics are summarized in Table 1. In brief, 20 eyes were selected from 10 human donors. The globes were enucleated and frozen according to a standard protocol. Donors were aged 41 to 74 years at time of death. Most donors were deceased due to a traffic accident, stroke, or cancer. The definitions of AMD and non-AMD retinas were based on both visual and histopathological examination, including the existence of drusen at the posterior pole and H&E staining. The associated retinal pigment epitheliums (RPEs) were isolated from non-AMD and AMD donors and cultured as primary RPEs. A detailed description of our RPE culture methods has been previously published (Bonnel et al., Exp Gerontol. 2003; 38(8):825-31). The cells were grown in Dulbecco's modified Eagle's medium containing nutrient mixture F12, 50/50 mix (Cellgro, Herndon, Va., USA) supplemented with 5% fetal bovine serum, 2-mM L-glutamine, 1-mM sodium pyruvate, 0.1-mM non-essential amino acids, penicillin (100 U/mL), and streptomycin (100 μg/mL). Cells were seeded onto tissue culture plates at a density of $2\times10^5$ cells/mL in complete medium and allowed to grow at 37° C. in a humidified environment of 5% $CO_2$ in air to reach about 80% confluence (1-2 days). The culture medium was then replaced with fresh serum-free medium containing penicillin (100 U/mL) and streptomycin (100 μg/mL) before treating the cells with various agents.

TABLE 1

Characteristics of Patients.

| Eye No. | Case No. | Age (yrs)/ Sex | Death Cause | Eye | Fundi | Relative Oct4 level | Relative SirT1 level |
|---|---|---|---|---|---|---|---|
| 1 | 1 | 74/M | T.A. | Right | AMD | 0.52 | 0.58 |
| 2 | | | | Left | AMD | 0.56 | 0.61 |
| 3 | 2 | 71/M | Cancer | Right | AMD | 0.61 | 0.67 |
| 4 | | | | Left | AMD | 0.55 | 0.63 |
| 5 | 3 | 66/M | T.A. | Right | AMD | 0.65 | 0.75 |
| 6 | | | | Left | AMD | 0.67 | 0.70 |
| 7 | 4 | 63/F | T.A. | Right | AMD | 0.68 | 0.76 |
| 8 | | | | Left | AMD | 0.63 | 0.72 |
| 9 | 5 | 61/M | Cancer | Right | AMD | 0.77 | 0.84 |
| 10 | | | | Left | AMD | 0.76 | 0.78 |
| 11 | 6 | 52/M | Stroke | Right | AMD | 0.89 | 0.91 |
| 12 | | | | Left | AMD | 0.84 | 0.88 |
| 13 | 7 | 72/M | T.A. | Right | Non-AMD | 0.85 | 0.91 |
| 14 | | | | Left | Non-AMD | 0.88 | 0.90 |
| 15 | 8 | 68/M | Stroke | Right | Non-AMD | 0.93 | 0.95 |
| 16 | | | | Left | Non-AMD | 0.9 | 0.93 |
| 17 | 9 | 59/F | T.A | Right | Non-AMD | 0.99 | 0.98 |
| 18 | | | | Left | Non-AMD | 0.95 | 0.98 |
| 19 | 10 | 41/M | T.A | Right | Non-AMD | 0.97 | 0.95 |
| 20 | | | | Left | Non-AMD | 1.0 | 1.0 |

AMD: Age-related macular degeneration;
T.A.: Traffic accident 1.2 Synthesis of Polyurethane and Short Branch PU-PEI (PU-PEI)

L-lysine-diisocyanate (LDI) 0.145 g (1) and N,N'-bis-(2-hydroxyethyl)-piperazine (PPA) 0.1024 g (2) were respectively dissolved in 1 mL anhydrous DMF solvent and mixed in a three-neck reaction flask under a dry nitrogen purge, heated at 60° C. and allowed to react for 12 hrs using a 0.5 wt % dibutyltin dilaurate catalyst. Then an excess amount of methanol (4 ml) was slowly added into the reaction mixture until no unreacted isocyanate was detected. The polyurethane was precipitated and purified in ethyl ether and dried at 40° C. under vacuum. The polymers were characterized by FT-IR and $^1$H NMR. $^1$H-NMR (400 MHz, DMSOd$_6$, ppm) δ: 2.50-2.71 (—N$_2$(CH$_2$CH$_2$)$_2$), 2.99, 3.9 (—NCH$_2$CH$_2$O—), 3.12 (—NHCH(COOCH$_3$)CH$_2$—), 1.21-1.81 (6H, —CH (COOCH$_3$)CH$_2$CH$_2$CH$_2$CH$_2$—), 2.90 (—CH$_2$CH$_2$NH—), 3.67 (—NHCOOCH$_3$), 3.4 (—COOCH$_3$), 8.01 (—NHCH (COOCH$_3$)CH$_2$—), 3.51 (—CH$_2$NHCOOCH$_3$). PU-sbPEI was synthesized using the aminolysis reaction of polyurethane (3) and small branch PEI (MW=600) (sbPEI) in FIG. 1. First, 0.1 g polyurethane was dissolved in 1 mL of anhydrous DMF and 0.6 g sbPEI (4) was dissolved in 0.5 mL MeOH with 1 mL Et$_3$N. Two solutions were mixed slowly and allowed to react at 45° C. for at least 48 hrs. The polymer was precipitated in an excess amount of anhydrous ethyl ether. Purification was performed by re-dissolving the above polymer in 3 mL MeOH and precipitating in 4 mL three times before vacuum-dried at 40° C. The polymer (PU-sbPEI) (5) was further characterized by FTIR and $^1$H NMR. PU-sbPEI: $^1$H-NMR (400 MHz, D$_2$O, ppm) δ: 2.48 (—N$_2$(—CH$_2$—CH$_2$)$_2$), 2.91 (—NCH$_2$CH$_2$O—), 3.99 (—NCH$_2$CH$_2$O—), 4.35 (—NHCH(CO—)CH$_2$—), 2.84, 1.32, 1.53 (—CHCH$_2$CH$_2$CH$_2$—), 2.91 (—CH$_2$CH$_2$NH—), 3.56 (—O—CH$_3$), 3.8 (—CONHCH$_2$—), 2.48, 3.14 (PEI:—CH$_2$—CH$_2$—), 3.51 (—CH$_2$NHCOCH—), 8.01 (—NHCH (CONH—)CH$_2$—), 0.95 (PEI:—NH—).

1.3 Delivery of Oct4 and SirT1 Genes by PU-sbPEI

The pcDNA3.1-SirT1 plasmid was a kind gift from Dr. Wenlong Bai (Yang et al., EMBO J. 2005; 24(5): 1021-32). The pMXs-hOct3/4 plasmid was purchased from Addgene (Cambridge, USA). The fragments of SirT1 cDNA and Oct3/4 cDNA was further subcloned into pEGFP-C1 vector (Clontech, USA). Oct4 and Sirt1 plasmids were dissolved in Opti-MEM medium with final concentrations of 1 g/L. DNA and PU-sbPEI (also denoted as PU) were mixed at a 5:1 ratio, and incubated for 30 min to form the DNA-PU-PEI complexes. Cells were grown to about 70% confluency prior to transfection. The complexes were added directly to cells, and were removed at 6 hours posttransfection. 48 hours later, cells were harvested and expression level of Oct4 and SirT1 were examined by RT-PCR and western blot.

1.4 Real-Time Reverse Transcription-Polymerase Chain Reaction (RT-PCR)

Real-time RT-PCR was performed as previously described (Chen et al., PLoS One. 2008; 3(7):e2637). For real-time RT-PCR, the total RNA was extracted using the RNAeasy kit (Qiagen, Valencia, Calif., USA) as manufacturer's instruction. Total RNA (1 g) of each sample was reversely transcribed in 20 μL using 0.5 g of oligo dT and 200 U Superscript II RT (Invitrogen, Carlsbad, Calif., USA). The amplification was carried out in a total volume of 20 μl containing 0.5 μM of each primer, 4 mM $MgCl_2$, 2 μl LightCycler™-FastStart DNA Master SYBR green I (Roche Molecular Systems, Alameda, Calif., USA) and 2 μl of 1:10 diluted cDNA. PCR reactions were performed on the ABI PRISM® 7900HT Sequence Detection System and the ABI Prism 5700 SDS (Applied Biosystems). In each experiment, the GAPDH housekeeping gene was amplified as a reference standard. The primers sequences of target genes were showed in Table 2. Reactions were prepared in duplicate and heated to 95° C. for 10 minutes followed by 40 cycles of denaturation at 95° C. for 10 seconds, annealing at 55° C. for 5 seconds, and extension at 72° C. for 20 seconds. All PCR reactions were performed in duplicate. Standard curves (cycle threshold values versus template concentration) were prepared for each target gene and for the endogenous reference (GAPDH) in each sample. To confirm the specificity of the PCR reaction, PCR products were electrophoresed on a 1.2% agrose gel.

TABLE 2

The primer sequences of RT-PCR.

| Gene (Accession No.) | Primer Sequence (5' to 3') | Product size (bp) | Tm (° C.) |
|---|---|---|---|
| Oct4 (NM_002701) | F: GTGGAGAGCAACTCCGATG (SEQ ID NO: 3)<br>R: TGCTCCAGCTTCTCCTTCTC (SEQ ID NO: 4) | 86 | 60 |
| SirT1 (AF083106) | F: CGTCTTATCCTCTAGTTCTTGTG (SEQ ID NO: 5)<br>R: ATCTCCATCAGTCCCAAATCC (SEQ ID NO: 6) | 175 | 55 |
| Oct4 (endo) (NM_002701) | F: GACAGGGGGAGGGGAGGAGCTAGG (SEQ ID NO: 7)<br>R: CTTCCCTCCAACCAGTTGCCCCAA AC (SEQ ID NO: 8) | 143 | 60 |
| Nanog (NM_024865) | F: ATTCAGGACAGCCCTGATTCTTC (SEQ ID NO: 9)<br>R: TTTTTGCGACACTCTTCTCTGC (SEQ ID NO: 10) | 76 | 60 |
| Klf4 (NM_004235) | F: AGGACCGCCACCCACACTTGT (SEQ ID NO: 11)<br>R: GGTCAGTTCATCTGAGCGGGCG (SEQ ID NO: 12) | 159 | 60 |
| SOX-2 (NM_003106) | F: CGAGTGGAAACTTTTGTCGGA (SEQ ID NO: 13)<br>R: TGTGCAGCGCTCGCAG (SEQ ID NO: 14) | 74 | 60 |
| CD44 (NM_000610) | F: TCACACAACAACACAAATGGCTGGT (SEQ ID NO: 15)<br>R: GCCCGTGGTGTGGTTGAAATGGT (SEQ ID NO: 16) | 168 | 60 |
| CD133 (NM_006017) | F: CGTGATTTTTTACTACCTGGGCTTA (SEQ ID NO: 17)<br>R: AGCCTCGGGTGGTCGG (SEQ ID NO: 18) | 77 | 60 |
| PAX6 (NM_000280) | F: GGGCCGAACAGACACAGCCC (SEQ ID NO: 19)<br>R: GCTGGGGACTGGGGGTTGCA (SEQ ID NO: 20) | 103 | 60 |
| PGC-1α (NM_013261) | F: AGATCGCCCTACAGCCGTCGG (SEQ ID NO: 21)<br>R: ACGGCGCTCTTCAATTGCCTT (SEQ ID NO: 22) | 159 | 60 |
| SOD1 (NM_000454) | F: TATGGCGACGAAGGCCGTGTG (SEQ ID NO: 23)<br>R: TGAGGACCTGCACTGGTACAGC (SEQ ID NO: 24) | 192 | 60 |
| SOD2 (NM_000636) | F: CCACGCGGCCTACGTGAACA (SEQ ID NO: 25)<br>R: TGGCTTCCAGCAACTCCCCT (SEQ ID NO: 26) | 200 | 60 |
| CAT (NM_001752) | F: GCTTCAGGGCCGCCTTTTTGC (SEQ ID NO: 27)<br>R: ATGCACATCGGGCCGTCACG (SEQ ID NO: 28) | 132 | 60 |
| GSH-Px (NM_000581) | F: TTTGGGCATCAGGAGAACGCCA (SEQ ID NO: 29)<br>R: GGGTCGGTCATAAGCGCGGT (SEQ ID NO: 30) | 200 | 60 |
| GAPDH (NM_002046) | F: AATTGAGCCCGCAGCCTCCC (SEQ ID NO: 31)<br>R: CCAGGCGCCCAATACGACCA (SEQ ID NO: 32) | 153 | 60 |
| Rat PGC-1α (NM_031347) | F: CGGGAGTCTGAAAGGGCCAAGC (SEQ ID NO: 33)<br>R: GTCCGCGTTGTGTCAGGTCTGA (SEQ ID NO: 34) | 104 | 60 |

TABLE 2 -continued

The primer sequences of RT-PCR.

| Gene (Accession No.) | Primer Sequence (5' to 3') | Product size (bp) | Tm (° C.) |
|---|---|---|---|
| Rat GAPDH (NM_017008) | F: GGGCTCTCTGCTCCTCCCTGTT (SEQ ID NO: 35)<br>R: AGGCGTCCGATACGGCCAAA (SEQ ID NO: 36) | 118 | 60 |

1.5 Western Blot Analysis and Immunofluorescence Assay

Cells were fixed, washed once in cold PBS, scraped, lysed with extraction buffer, and centrifuged at 10,000 rpm (9,730 g) for 10 minutes to remove insoluble material. Protein concentrations were determined using a protein assay kit (Bio-Rad, Hercules, Calif., USA). Cell extracts in sample buffer were placed in boiling water for 5 minutes and then separated by 10% SDS-PAGE gel. After electrophoresis, the gel was transferred onto a PVDF membrane for immunoblotting. The membrane was blocked by incubation in non-fat milk at room temperature for 0.5 hour and incubated with SirT1 antibody (1:1000; Santa Cruz Biotechnology, Santa Cruz, Calif., USA), Oct4 antibody (1:500; Santa Cruz Biotechnology) for 16 hours at 4° C., washed five times with tris-buffered saline tween-20 (TBST), and incubated at room temperature with horseradish peroxidase-conjugated secondary antibody for 2 hours. The membrane was washed six times with TBST, and specific bands were made visible by chemiluminescence (ECL, Santa Cruz). For immunofluorescence study with nestin and musashi, the spheroid body were immunostained with monoclonal antibodies against nestin (1:500; DAKO) and musashi (1:500; Chemicon) diluted in PBS/3% Triton X-100/10% normal goat serum (NGS), and individually incubated with the coverslips for 2 hours at 37° C. Coverslips were washed three times (10 minutes each) in PBS and incubated in appropriate secondary antibodies (1:200; Sigma, St Louis, Mo., USA) for 30 minutes at 37° C. Coverslips were rinsed three times in PBS and one time in distilled water and mounted on glass slides with Fluoesave (Calbiochem, La Jolla, Calif., USA). The number of nestin and musashi-positive cells was assessed in 10 non-overlapping fields for each sphere. The total number of cells in each field was determined by counterstaining cell nuclei with 4,6-diamidine-2-phenylindole dihydrochloride (DAPI; 1 mg/mL).

1.6 Microarray Analysis and Bioinformatics

Total RNA was extracted from cells using Trizol reagent (Life Technologies, Bethesda, Md., USA) and the Qiagen RNAeasy (Qiagen, Valencia, Calif., USA) column for purification. cRNA probe preparation, array hybridization and data analysis were done as accord with the recommendations of the Affymetrix™. The Affymetrix HG-U133 Plus 2.0 whole genome chips were used. RMA log expression units were calculated from Affymetrix GeneChip array data using the 'affy' package of the Bioconductor website suite of software for the R statistical programming language. The default RMA settings were used to background correct, normalize and summarize all expression values. Significant difference between sample groups was identified using the 'limma' package of the Bioconductor. Briefly, a t-statistic was calculated as normal for each gene and a p-value then calculated using a modified permutation test. To control the multiple testing errors, a false discovery rate (FDR) algorithm was then applied to these p-values to calculate a set of q-values: thresholds of the expected proportion of false positives, or false rejections of the null hypothesis. Heatmap was created by the dChip software. Principle component analysis (PCA) was performed also by the dChip software to provide a visual impression of how the various sample groups are related. Gene annotation and gene Ontology were performed by the DAVID Bioinformatics Resources 6.7 interface. For obtaining functional regulatory networks, filtrated features from array analysis will be subjected into the plug-in of Cytoscape software. The knowledge base behind Cytoscape was built upon scientific evidence, manually collected from thousands of journal articles, textbooks, and other data sources. After a list of signature genes was uploaded, interaction among focus genes and interaction among interacting genes and molecules from the knowledge base are used to combine genes into networks according to their probability of having more focus genes than expected by chance. The term "network" in Cytoscape is not the same as a biological or canonical pathway with a distinct function but a reflection of all interactions of a given protein as defined in the literature.

1.7 Bisulfite Sequencing

Bisulfite reaction was performed using the Imprint DNA Modification Kit (Sigma) according to the manufacturer's instruction. 500 nanograms of genomic DNA were used for each one-step modification reaction. Post-modified DNA was cleaned up and amplified by PCR using primers as described previously (Coleman et al., Lancet. 2008; 372(9652):1835-45; and Ding et al., Prog Retin Eye Res. 2009; 28(1):1-18). PCR products were cloned into pGEM-T Easy vector (Promega), and 10 randomly selected clones for each sample were sequenced.

1.8 Determining the Malondialdehyde (MDA) Level and Superoxide Dismutase (SOD), Glutathione Peroxidase (GSH-Px), and Catalase (CAT) Activity The level of MDA was determined by the double-heating method of Draper and Hadley (Simonelli et al., Mol. Ther. 2010; 18(3):643-50). The results were expressed as nmol/g protein. Total SOD activity was determined by Superoxide Dismutase Activity Colorimetric Assay Kit (Abcam) according to manufacturer's protocol. SOD activity was expressed as units/g protein. GSH-Px and CAT activities were measured by glutathione peroxidase cellular activity assay kit and catalase assay kit, both are purchased from Sigma. GSH-Px and CAT activity values were given in units/g protein and μmoles/min/g protein (Maguire et al., N Engl J. Med. 2008; 358(21): 2240-8).

1.9 Determination of Intracellular Reactive Oxygen Species (ROS) Production and Glutathione (GSH) Content Cultured aRPE cells were washed with PBS twice and treated with 100 μM $H_2O_2$. After 8 hours, the medium was removed, and the cells were collected for the subsequent experiments. The measurement of intracellular ROS production by the probe 2',7'-dichlorofluorescein diacetate (DCFH-DA; Molecular Probes, Eugene, Oreg., USA) was mentioned previously (Thomas et al., Nat Rev Genet. 2003; 4(5):346-58). In brief, cells were incubated with 5 mol/L DCFH-DA in culture medium for 30 min at 37° C., followed by washing with PBS and flow cytometric analysis. The intracellular GSH content was detected by colorimetric assay using the GSH-400 kit (OXIS International, Portland, Oreg., USA). In the GSH-400 assay, 4-chloro-1-methyl-7-trifluoromethyl-quinolinium methylsulfate was added to react with all mercaptans in the sample, leading to the formation of substitution products, thioesters. Then, 30% sodium hydroxide was used to mediate a β-elimination reaction and specifically transform GSH-thioester into a chromophoricthione with a maximal absorbance wavelength at 400 nm that was detected by a spectrophotometer.

1.10 Animals and Oct4/SirT1 Gene Delivery

All experiments were performed in compliance with the Animal Care and Use Committee guidelines and in accordance with the ARVO Statement for the Use of Animals in Ophthalmic and Vision Research. All efforts were made to minimize the number of animals used and their suffering. Four-week-old, male, Sprague-Dawley rats, each weighing 150 to 250 g, were housed in plastic cages in a climate-controlled animal facility and kept under dim cyclic light (5 lux, 12 hours on/off). All animals had free access to food and water. Rats were anesthetized with intramuscular injections of 0.15 mL/kg of an equal-volume mixture of 2% lidocaine (Xylocalne; Astra, Södertälje, Sweden) and 50 mg/mL ketamine (Ketalar; Parke-Davis, Morris Plains, N.J., USA). After the rats were anesthetized, the corneas were anesthetized with a drop of 0.5% proparacaine hydrochloride (Alcaine; Alcon-Couvreur, Puurs, Belgium), pupils were dilated with 1% tropicamide (1% Mydriacyl; Alcon Laboratories, Hempstead, UK) and then the eyes were gently protruded with a rubber sleeve. Gene delivery was performed as described elsewhere, with modifications (Wu et al., Invest Ophthalmol V is Sci. 2002; 43(11):3480-8). Briefly, a superior temporal periotomy was made, and a sclerotomy was performed 1 mm behind the limbus with the tip of a 30-gauge needle. A 33-gauge blunt-tip needle (Hamilton, Reno, Nev., USA) was inserted subretinally, and 5 μL PU-PEI-OS mixture was injected by leaving the needle for 1 minute to reduce the reflux and was identified by formation of a retinal bleb. The eyes were discarded when massive subretinal hemorrhage developed. Similarly, the contralateral eye was injected with PU-vector as the control.

1.11 Light Exposure

Light exposure experiments were performed as described previously (Wenzel et al., Prog Retin Eye Res. 2005; 24(2): 275-306) with slight modification 2 weeks after subretinal delivery of PU particles. The rats were exposed to 10,000 lux of white light for 2 hours from 9:00 AM in a Plexiglas cage having mirrors at the lateral side and floors. Before intense light exposure, rats were dark adapted for 24 hours. The pupils were dilated with 1% tropicamide (1% Mydriacyl; Alcon) before light exposure. The inside temperature of the cage was maintained at 24° C. Immediately after 2-hour exposure to light, the rats were maintained under dim cyclic light (5 lux, 12 hours on/off). For histologic and immunohistologic analyses, the animals were sacrificed by carbon dioxide suffocation 3 days, 5 days, and 2 weeks after the start of light exposure, and the eyes were then enucleated. For western and enzyme activity analyses, the retinas at these time points were harvested for determination of Oct4 and SirT1 levels, as well as malondialdehyde (MDA) levels and superoxide dismutase (SOD), glutathione peroxidase (GSH-Px), and catalase (CAT) activities.

1.12 Measurement of Outer Nuclear Layer (ONL) Thickness

Rats were sacrificed in a carbon dioxide-saturated chamber, perfused with 10 ml of PBS 3 days, 5 days and 2 weeks after light exposure. Paraffin-embedded retinal sections (3 μm) from enucleated eyes were prepared and stained with hematoxylin and eosin (H&E). For each section, digitized images of the entire retina were captured with a digital imaging system at 4× magnification with 1300×1030 pixels. To cover the entire retina, five images were obtained from each section. The ONL thickness were measured at 0.5, 1.0, 1.5, 2.0, and 2.5 mm superior and inferior to the optic nerve head (ONH) and at the periphery, 100 μm from the inferior and superior edges of the retina, with Image J software. The ONL areas were calculated by integrating the area under the thickness histogram from 2.5 mm superior and 2.5 mm inferior to the ONH.

1.13 Electroretinography (ERG)

The animals were dark-adapted for at least a 24-hour period overnight, and ERGs were recorded at 3 days, 5 days, or 2 weeks after light exposure, as previously described with modifications (Peng et al., Biomaterials. 2010; 31(7): 1773-9). Briefly, the animals were anesthetized with intramuscular injections of 50 mg/kg ketamine/0.15 mg/kg lidocaine, the corneas were anesthetized with a drop of 0.5% proparacaine hydrochloride, and the pupils were dilated with 1% tropicamide. The rats were placed on a heating pad that maintained their body temperature at 35-36° C. throughout the experiment. The ground electrode was a subcutaneous needle in the tail, and the reference electrode was placed subcutaneously between the eyes. The active contact lens electrodes were placed on the cornea. Responses were amplified differentially, light pulses of 800 cds/m$^2$, bandpass filtered at 0.3 to 500 Hz, digitized at 0.25- to 0.5-ms intervals by a commercial system (RETIport ERG laptop version, Acrivet, Germany), and stored for processing. The amplitude of the a-wave was measured from the baseline to the trough of the a-wave, and b-wave amplitude was determined from the trough of the a-wave to the peak of the b-wave. The implicit times of the a- and b-waves were measured from the onset of stimuli to the peak of each wave.

1.14 Statistical Analysis

The results are expressed as mean±SD. Statistical analyses were performed using the t-test for comparing two groups, and one-way or two-way ANOVA, followed by Bonferroni's test, was used to detect differences among three or more groups. The correlation between expression levels and age were analyzed by the Pearson's correlation coefficient and unpaired Student t test. Results were considered statistically significant at $P<0.05$. All analyses were performed using SPSS 12.0.

2. Results 2.1 Self-Renewal Ability of the Cells Transfected by Oct4 and SirT1

Figure 2:
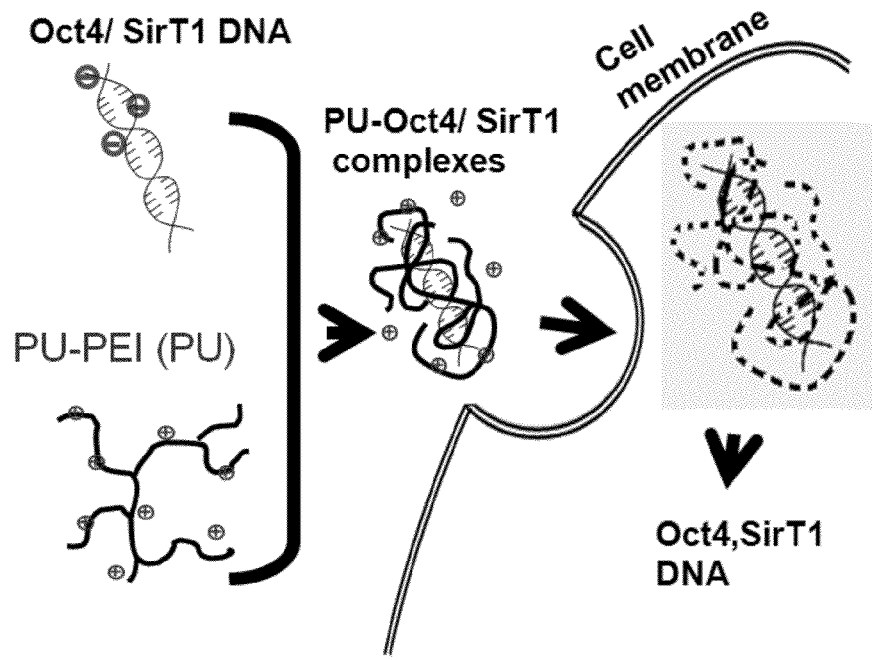
FIG. 2 provides (A) a schematic diagram of the transfection of PU-PEI into cells and (B) photographs of the primary aRPE cells transfected with PU-PEI carrying the cDNA for Oct4 and SirT1 or empty vector, wherein cells transfected with empty vector were shown in the left panel (aRPE-PU); and cells co-transfected with Oct4 and SirT1 were shown in the middle (aRPE-PU-OS #1) and right (aRPE-PU-OS #2) panels as two independent stable clones (Bar=50 μm).
Figure 2:
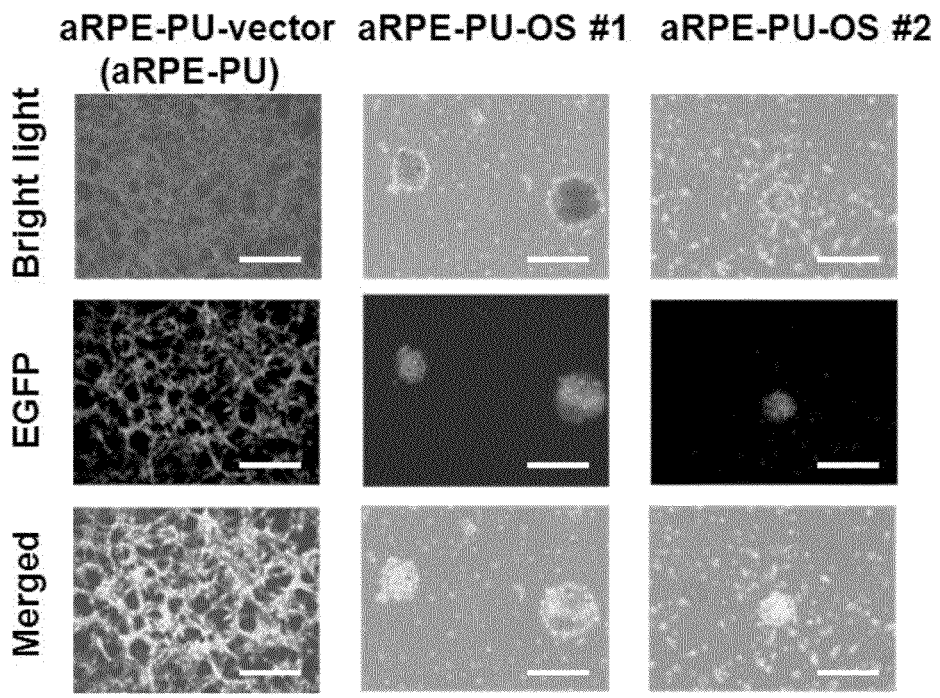
Figure 3:
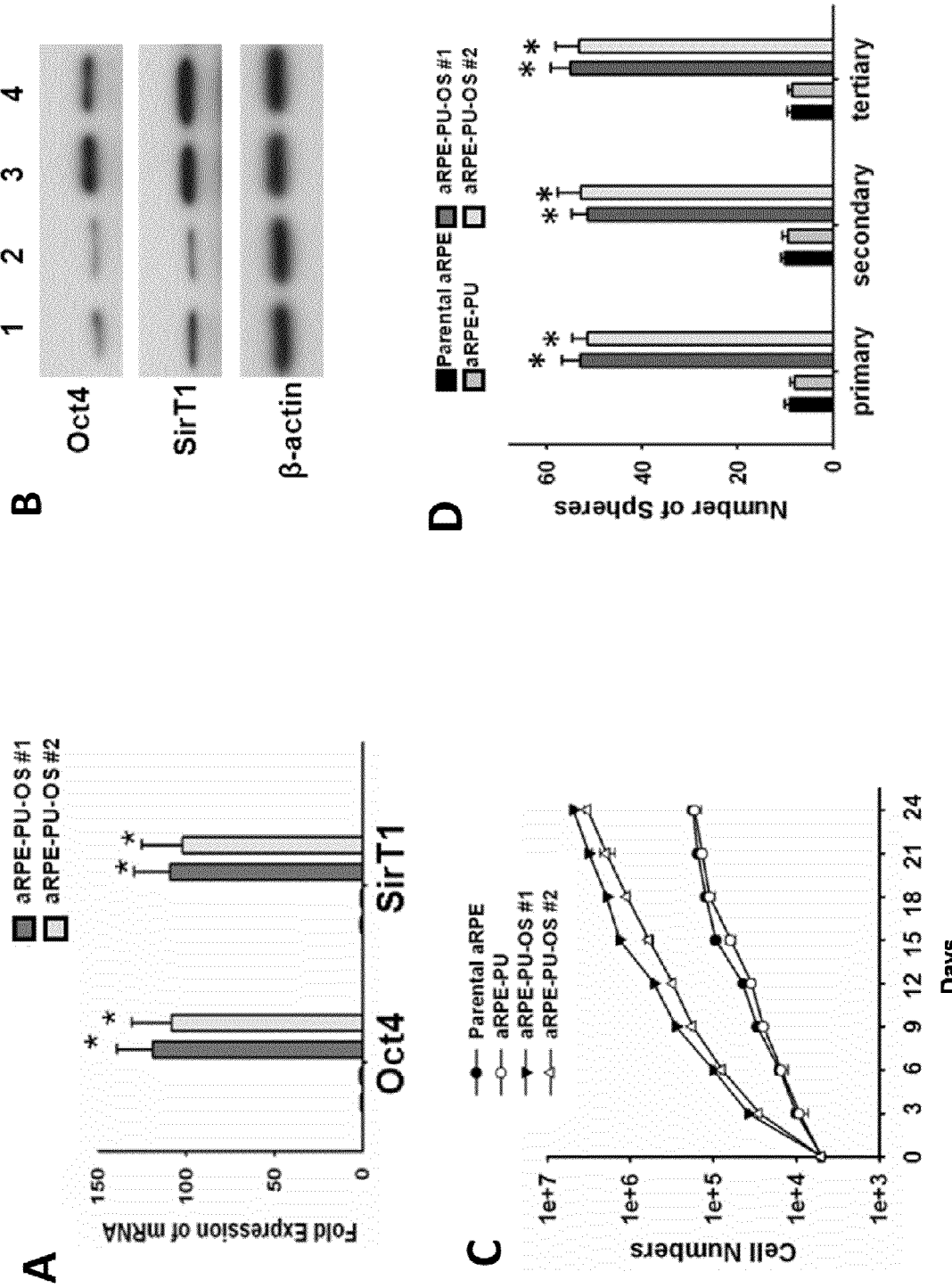
FIG. 3 provides the results of transfection with PU-PEI in aRPE cells, wherein (A) shows quantitative RT-PCR analysis of Oct4 and SirT1 expression in aRPE-PU-OS #1 and aRPE-PU-OS #2 clones as compared with parental aRPE cells; (B) shows the protein levels of Oct4 and SirT1 analyzed by western blot (lane 1: parental aRPE, lane 2: aRPE-PU, lane 3: aRPE-PU-OS #1, lane 4: aRPE-PU-OS #2); (C) shows the growth curve of parental aRPE, aRPE-PU, and two aRPE-PU-OS clones over 24 days; and (D) shows the results of sphere formation assays; wherein the spheres generated by two aRPE-PU-OS clones, aRPE-PU, and aRPE cells in three passages were quantified. Parental aRPE cells served as controls (*p<0.05; data shown are the mean±SD of three independent experiments).

Retinal degeneration, such as age-related macular degeneration (AMD), has become a major cause of blindness worldwide. Oxidative stress-induced damage has been proposed to be a major risk of AMD (Coleman et al., Lancet. 2008; 372(9652):1835-45) because the retina is highly susceptible to damage by reactive oxygen species (ROS). Oxidative cell damage with persistent chronic inflammation has been shown to gradually result in permanent photoreceptor loss and retinal pigment epithelium (RPE) dysfunction in advanced AMD (Ding et al., Prog Retin Eye Res. 2009; 28(1): 1-18). RPEs are able to maintain the physiology of the neurosensory retina. The possible rescuing role of Oct4/SirT1 was examined by overexpressing these two factors in aged retinal pigment epithelium (aRPE). Polyurethane-short branch polyethylenimine (PU-PEI, also denoted as PU) is not cytotoxic and has high transfection efficiency (Hung et al., J Control Release. 2009; 133(1):68-76; and Liu et al., Biomaterials. 2009; 30(34):6665-73). In this study, stable Oct4/SirT1-overexpressing aRPE (aRPE-PU-OS) cells were generated from primary aRPEs derived from donor No. 7 (the oldest non-AMD donor) using the PU-PEI delivery system (FIG. 1) with plasmid vectors encoding EGFP, Oct4, and SirT1 cDNA. Empty vector-delivery control cells (aRPE-PU) were produced simultaneously. A schematic figure of PU-PEI-mediated gene delivery is shown in FIG. 2A. Delivery efficiency, as evaluated by the proportion of EGFP-positive cells, was approximately 70%. Interestingly, Oct4/SirT1 co-overexpression caused aRPE-PU cells to form spheroid-like bodies in two stable clones, aRPE-PU-OS#1 and aRPE-PU-OS#2, whereas the control cells had no signs of spheroid-like bodies (FIG. 2B). Quantitative RT-PCR and western blotting confirmed the overexpression of Oct4 and SirT1 mRNA (FIG. 3A) and protein (FIG. 3B) levels in two aRPE-PU-OS clones, respectively. The proliferation rate was also increased in aRPE-PU-OS cells compared to the parental aRPEs and the aRPE-PU cells over 24 days (FIG. 3C). Because sphere formation is a key behavior for evaluating the self-renewal ability of progenitor cells (Peng et al., Eur Neuropsychopharmacol. 2008; 18(2):128-40), the ability to successfully form spheres after serial passaging was examined. Notably, after serial passages in serum-free medium, aRPE-PU-OS cells maintained a high sphere-forming ability (FIG. 3D). These data demonstrated the increased self-renewal ability of aRPE cells after the ectopic overexpression of Oct4 and SirT1.

2.2 Progenitor-Like Features of the Cells Transfected by Oct4 and SirT1

Figure 4:
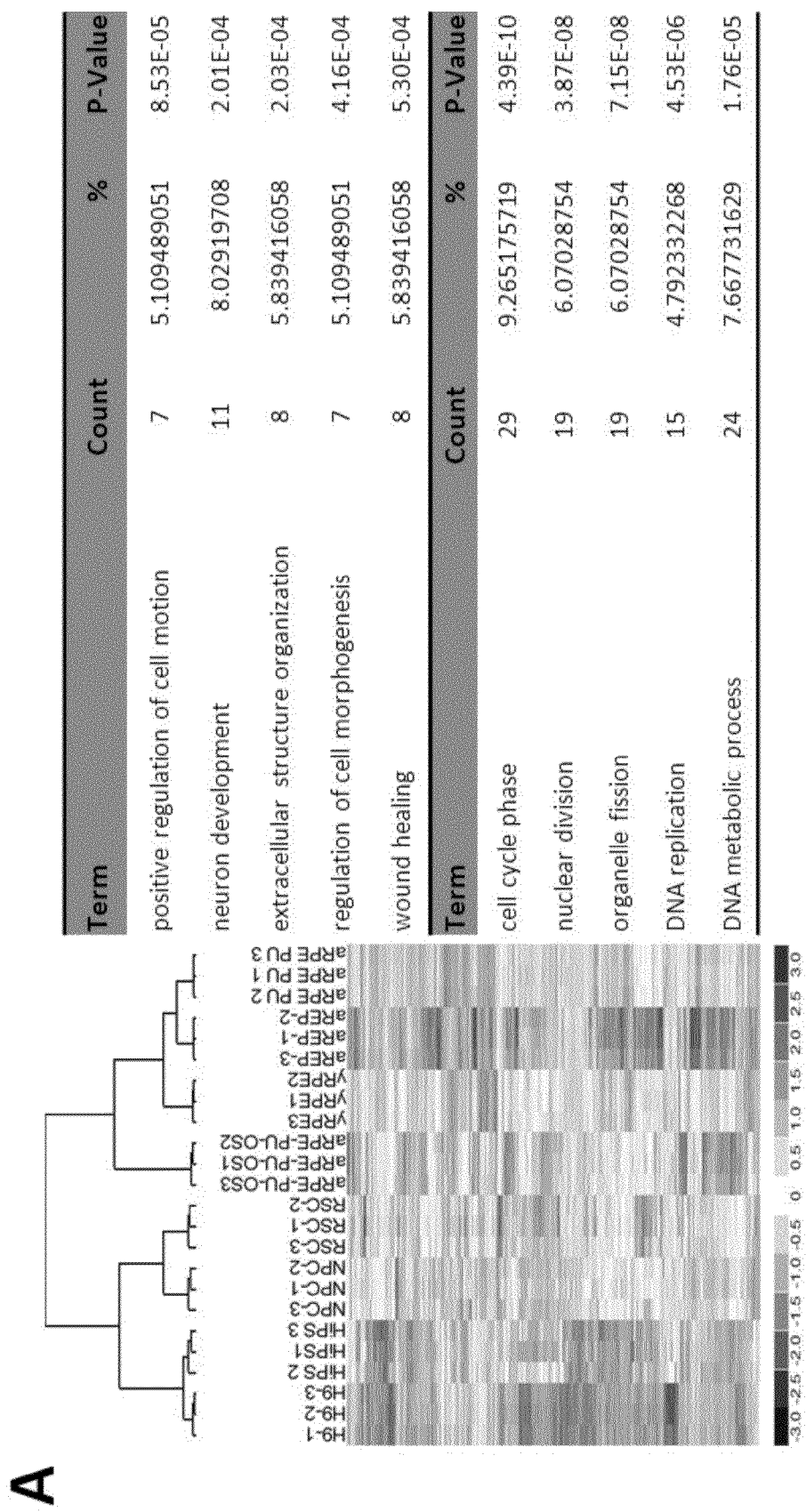
FIG. 4 provides the results of Oct4 and SirT1 promoting the reprogramming of aRPE cells into retinal progenitor-like cells, wherein (A) shows the gene expression microarray analysis (gene tree) of the 500 probe sets that were differentially expressed in aRPE-PU-OS cells as compared to aRPE-PU cells, demonstrated by a hierarchy heat map; the time-dependent changes in the expression of the 500 probe sets were presented as a log scale of the expression values provided by the R statistical programming language software; (B) shows the results of principal component analysis (PC1: vertical axis; PC2: horizontal axis; Unit: D-chip unit) being used to measure the expression profiling using bioinformatics methods; (C) shows the results of quantitative RT-PCR analysis of stem cell-related gene expression using parental aRPE cells as controls; and (D) shows the bisulfite sequencing of DNA methylation profile of the Oct4 promoter in aRPE-PU, SirT1-overexpressing aRPE (aRPE-PU-SirT1), Oct4-overexpressing aRPE (aRPE-PU-Oct4), and aRPE-PU-OS cells; open circles indicate unmethylated dinucleotides, and filled circles indicate methylated CpG dinucleotides; (E) shows the results of quantification of the methylation state of the Oct4 promoter; (F) shows the levels of transcripts of endogenous (endo) Oct4 analyzed by qRT-PCR with endogenous gene-specific primers; total RNA was extracted from aRPE cells, aRPE-PU cells, two aRPE-PU-OS clones, and the human embryonic stem cell line H9; (G) shows the results of average distance analysis; average lineage transcriptome distance analysis was used to demonstrate the distance from H9 ("HiPS" represents human induced pluripotent stem cells; "NPC" represents neural progenitor cells; "RSC" represents retinal stem cells, and "yRPE" represents young retinal pigment epithelium); and (H)-(I) show the results of immunofluorescence analyses of the expression of Nestin (H) and Musashi (I) in aRPE-PU-OS cells in comparison with those in parental and control aRPE-PU cells (*$p<0.05$; ns, not significant ($p>0.05$); data shown are the mean±SD of three independent experiments).
Figure 4:
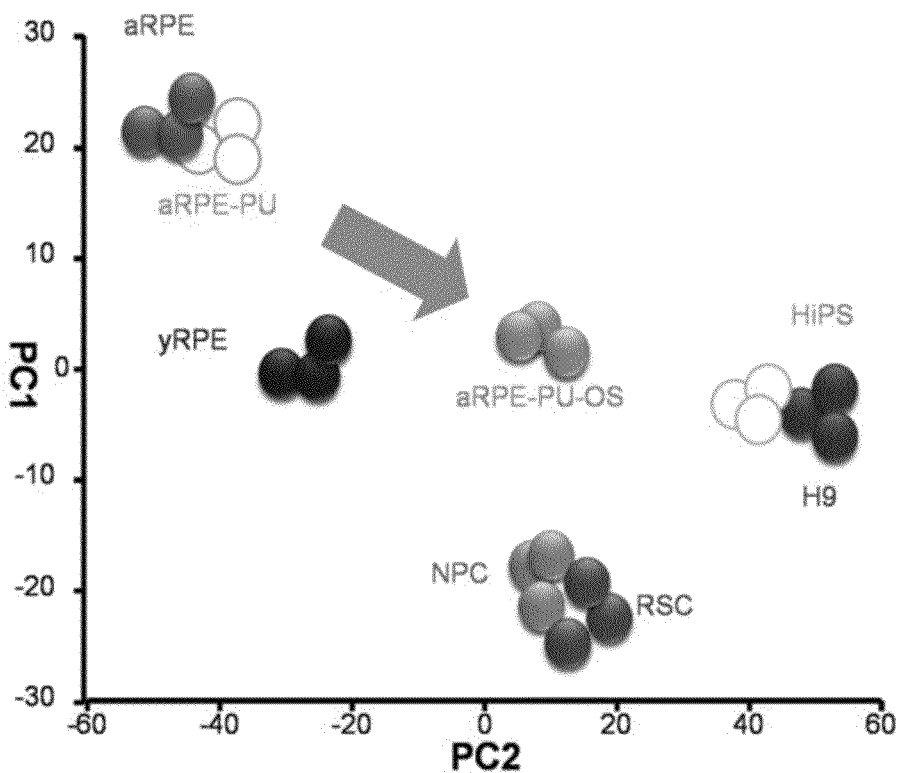
Figure 4:
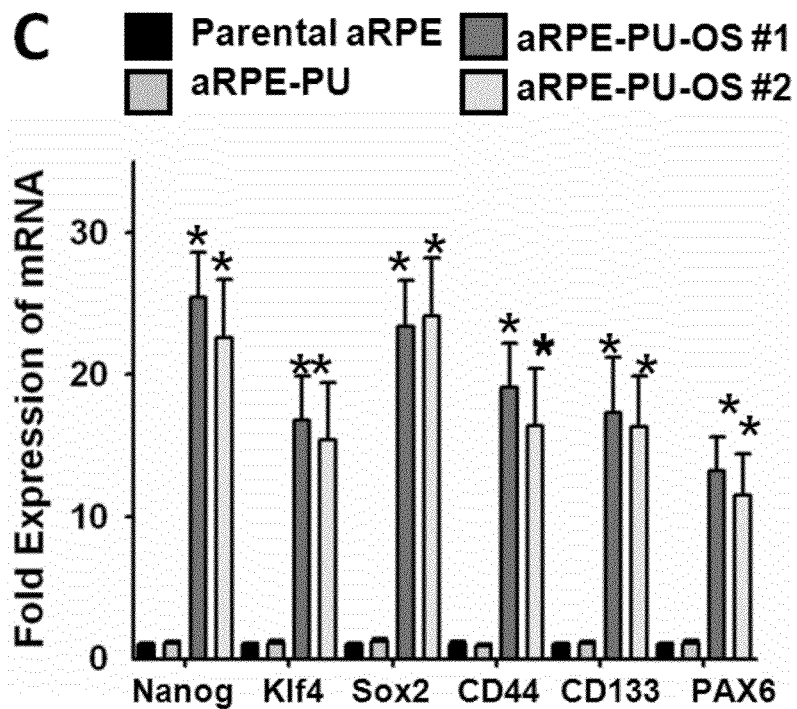
Figure 4:
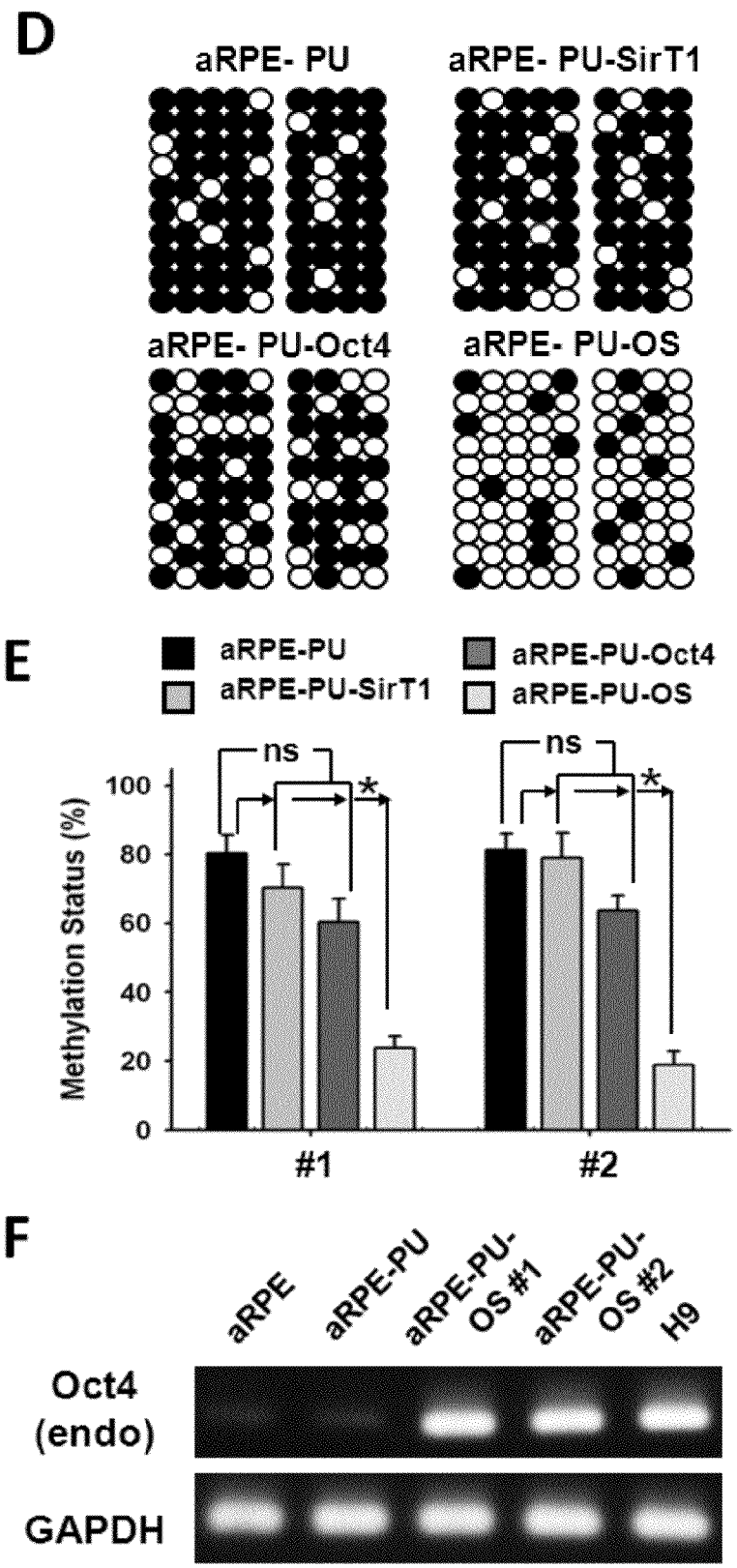
Figure 4:
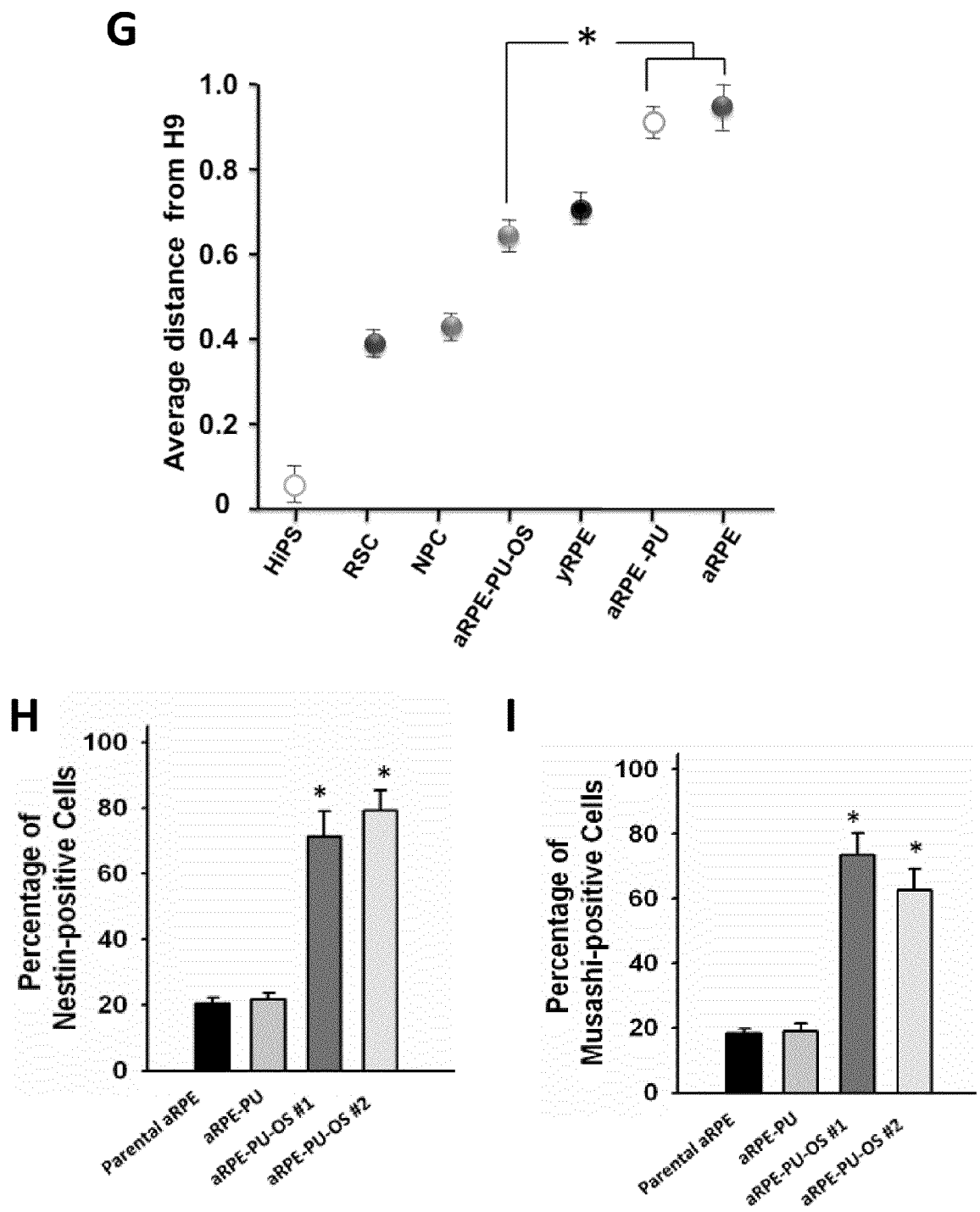

The genomic traits of aRPE-PU-OS cells and aRPE-PU control cells were further examined using gene expression microarray analysis. The gene expression profiles and Gene Ontology (GO) database showed that the expression of 500 probe sets was significantly altered in aRPE-PU-OS cells compared with the parental aRPEs or the aRPE-PU cells when examined using the hierarchical clustering method (FIG. 4A, left panel). The predominantly upregulated processes in aRPE-PU-OS cells included those pertaining to neural development, regulation of cell morphogenesis, extracellular structure organization, cell mobility and wound healing (FIG. 4A, right upper panel). In contrast, downregulated genes included those related to nuclear division, organelle fission and DNA replication (FIG. 4A, right lower panel). The microarray data demonstrated that Oct4 and SirT1 co-overexpression promoted the aRPE gene pattern to shift toward retinal progenitors based on principle component analysis (FIG. 4B). Moreover, the average distance analysis showed that the gene expression pattern of aRPE-PU-OS cells was more similar to that of retinal progenitor cells but was dissimilar to the aRPE-PU cells and the parental aRPEs (FIG. 4G). Notably, several stem cell- and retinal progenitor-related genes, including Nanog, Klf-4, Sox2, CD44, CD133 and Pax6, were also upregulated in aRPE-PU-OS cells, as compared to aRPE-PU cells (FIG. 4C). Furthermore, the quantification of immunofluorescence showed that the neural progenitor markers Nestin (FIG. 4H) and Musashi (FIG. 4I) were significantly increased in both aRPE-PU-OS clones as compared with the parental and aRPE-PU cells. A low degree of DNA methylation in the promoter region of pluripotency regulators, such as Oct4, is representative of stem cells or reprogramming pluripotent stem cells (Okita et al., Nature. 2007; 448(7151):313-7; and Mikkelsen et al., Nature. 2008; 454(7200):49-55). Because the aRPE-PU-OS gene expression pattern shifted toward that of retinal precursor-like cells, we further validated the changes in the methylation pattern of the Oct4 promoter in aRPE-PU-OS cells and aRPE-PU cells with the overexpression of only Oct4 or SirT1 (aRPE-PU-Oct4 and aRPE-PU-SirT1, respectively). Bisulfite sequencing results showed a much lower methylation status in the Oct4 promoter of aRPE-PU-OS cells as compared with aRPE-PU cells (FIG. 4D). Notably, ectopic expression of SirT1 or Oct4 alone did not significantly reduce the methylation level of the Oct4 promoter in aRPE-PU cells (FIGS. 4D and 4E). Using primers specifically targeting endogenous but not exogenous Oct4 transcripts, qRT-PCR demonstrated that exogenous expression of Oct4 and SirT1 induced endogenous Oct4 transcription (FIG. 4F). This finding supported the hypothesis that Oct4/SirT1 co-overexpression had synergistic effects that enhanced Oct4 promoter activity partly through a demethylation mechanism in aRPE cells, resulting in the upregulation of Oct4 downstream target genes.

2.3 Antioxidative Properties in aRPE-PU-OS Cells

Figure 5:
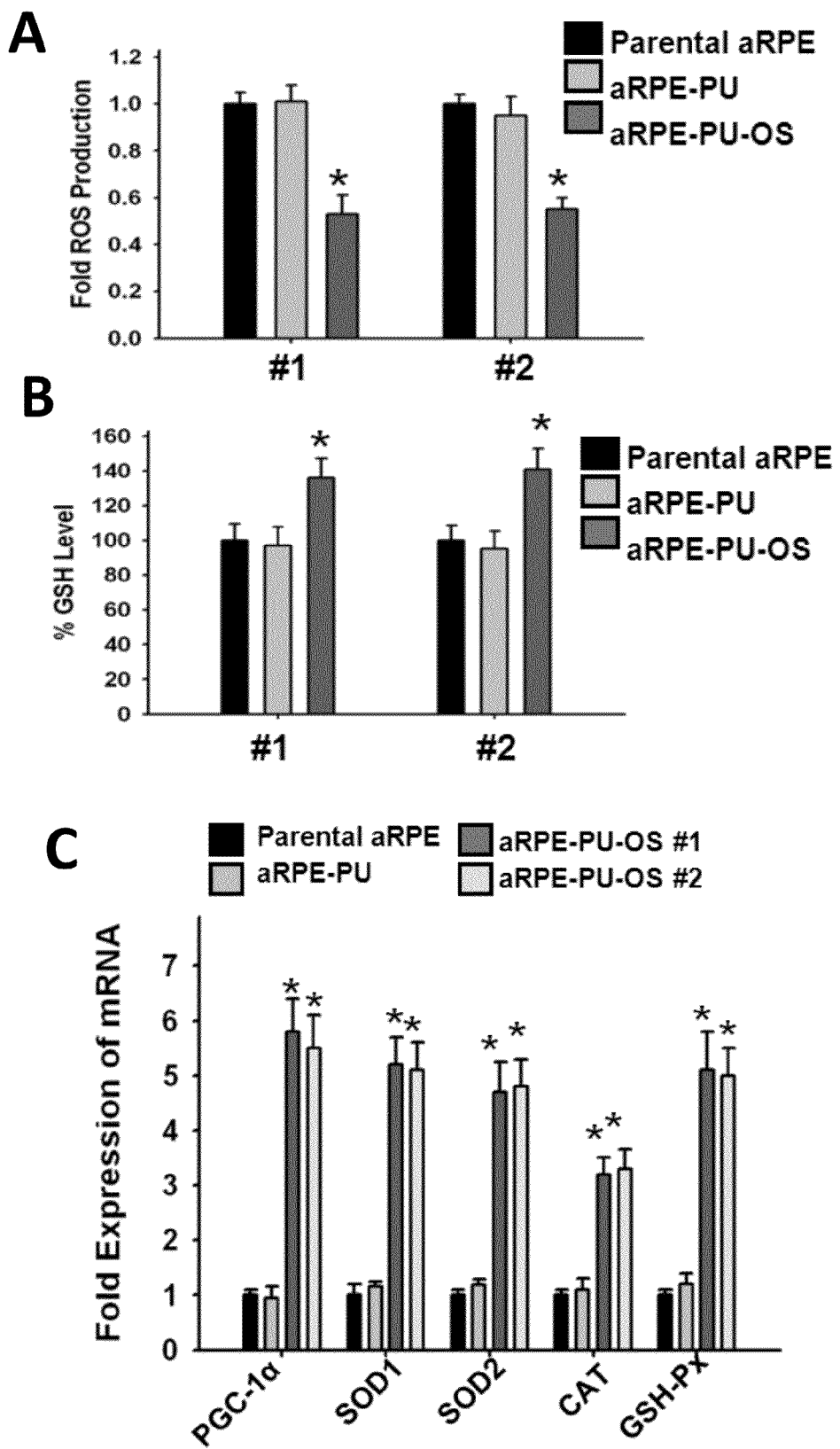
FIG. 5 provides the results of Oct4-SirT1 co-overexpression inducing antioxidant effects in aRPE cells, wherein (A) shows the intracellular ROS level in aRPE-PU cells and two aRPE-PU-OS clones determined by flow cytometry; (B) shows the glutathione (GSH) level (% of control) detected by flow cytometry; and (C) shows the quantitative RT-PCR analysis of antioxidation genes. Parental aRPE cells served as controls (*$p<0.05$; data shown are the mean±SD of three independent experiments).

A literature-based network analysis of all MEDLINE records (title and abstract) and Cytoscape software were used to group the target-linkage genes from our microarray data using a Natural Language Processing (NLP) regimen for gene and protein names. Network genes that were involved in Pou5f1 (Oct4), SirT1, Nanog, Pax6, and ppargc1a (PGC-1α) in aRPE-PU-OS cells but not in aRPE-PU cells were identified (data not shown). Flow cytometry analysis indicated that intracellular ROS levels were decreased and maintained at low levels in aRPE-PU-OS cells as compared with aRPE-PU cells (FIG. 5A). In contrast, the GSH levels of aRPE-PU-OS cells were significantly higher than those of the parental aRPE or aRPE-PU cells (FIG. 5B). Consistent with the microarray analysis results showing an upregulation of the PGC-1α gene, qRT-PCR revealed that the expression levels of PGC-1α and several antioxidant enzymes, such as SOD1, SOD2, CAT, and GSH-Px, were highly increased in both RPE-PU-OS clones ($p<0.05$; FIG. 5C).

Figure 6:
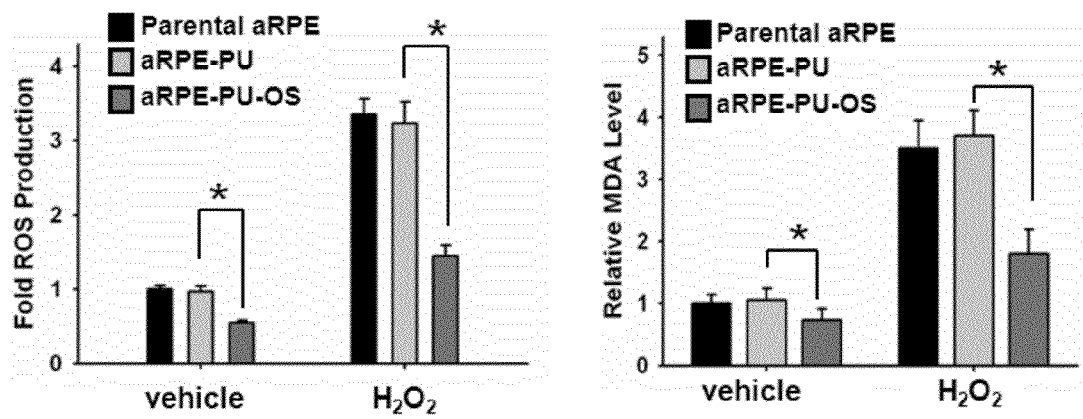
FIG. 6 provides the results of Oct4-SirT1 co-overexpression inducing antioxidant effects in aRPE cells with $H_2O_2$ treatment, wherein (A) shows the intracellular ROS levels (left) and the relative change in MDA activity (right) determined after cells were exposed to 100 µM $H_2O_2$ for 8 hours; (B) shows the glutathione (GSH) levels (% of control, left upper), relative changes in SOD (right upper), CAT (left lower), and GSH-Px (right lower) activities determined after the cells were exposed to 100 µM $H_2O_2$ for 8 hours; (C) shows qRT-PCR quantifying the relative amounts of the antioxidation genes in the indicated groups after cells were exposed to 100 µM $H_2O_2$ for 8 hours; and in (D)-(E), the cells were pretreated with or without 1 mmol/L BSO (a γ-glutamylcysteine synthetase inhibitor) and 0.5 mmol/L Tempol (a membrane-permeable radical scavenger) followed by 100 µM $H_2O_2$ 24 h later, and the ROS production (fold of control) (D) and the survival rate (% of control) (E) were determined after another 8 hours (#$p<0.05$; *$p<0.05$; ns, not significant ($p>0.05$); data shown are the mean±SD of three independent experiments).
Figure 6:
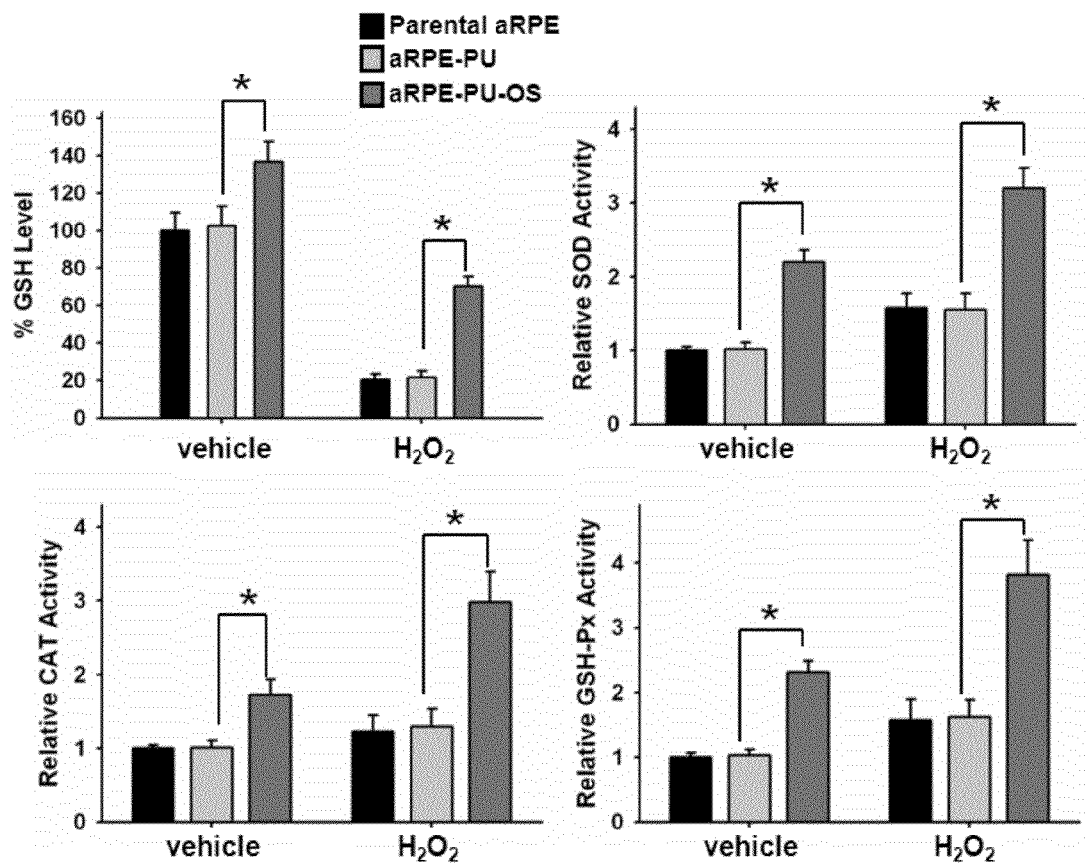
Figure 6:
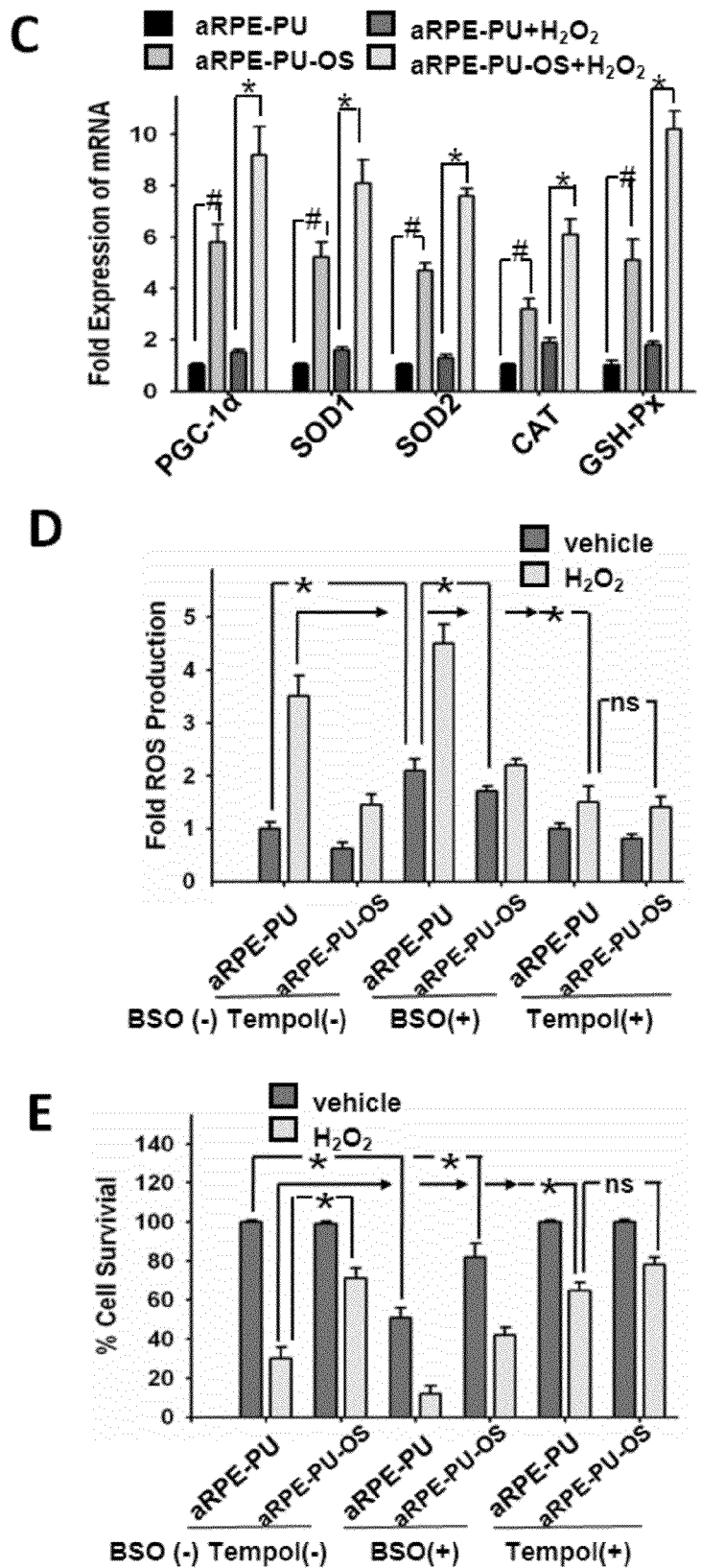

To further describe the antioxidant properties induced by overexpression of Oct4/SirT1, $H_2O_2$ was used to induce oxidative damage in aRPE-PU and aRPE-PU-OS cells. aRPE-PU-OS cells exhibited lower basal intracellular ROS and MDA levels than aRPE-PU cells (FIG. 6A, left and right, respectively). $H_2O_2$ treatment significantly increased both ROS and MDA levels, and the $H_2O_2$-induced elevation of both oxidative substances was significantly decreased in the aRPE-PU-OS cells (FIG. 6A, left and right, respectively). In addition, GSH levels and the activity of three antioxidant enzymes, SOD, CAT and GSH-Px, were significantly increased in the aRPE-PU-OS cells in both basal and $H_2O_2$-treated conditions (FIG. 6B, left upper, right upper, left lower and right lower, respectively). Notably, PGC-1α and ROS-scavenger gene levels were increased in the aRPE-PU-OS cells, and the expression of all of these genes was further enhanced by $H_2O_2$ (FIG. 6C). The antioxidative effects of Oct4/SirT1 overexpression were confirmed by challenging cells with an endogenous ROS generator, 1-S,R-buthionine sulfoximine (BSO; Sigma), a selective inhibitor of γ-glutamylcysteine synthetase. The aRPE-PU-OS cells were found to have reduced ROS production and decreased cell death upon BSO treatment (FIGS. 6D and 6E). Moreover, pretreatment of cells with 4-hydroxy-2,2,6,6-tetramethylpiperidinyloxy (Tempol; Sigma), a membrane-permeable radical scavenger, decreased $H_2O_2$-induced ROS production and cell death in the aRPE-PU cells ($p<0.05$ between the Tempol/$H_2O_2$ and $H_2O_2$ groups; FIGS. 6D and 6E), but Tempol treatment in the aRPE-PU-OS cells did not further enhance the Oct4/SirT1-dependent antioxidative and cytoprotective effects compared to aRPE-PU cells ($p>0.05$ between the aRPE-PU-OS/Tempol/$H_2O_2$ and aRPE-PU/Tempol/$H_2O_2$ groups; FIGS. 6D and 6E). These data suggest that the cytoprotective effect of aRPE-PU-OS was mediated by a reduction in oxidative stress. Taken together, aRPE-PU-OS cells exhibited significantly higher antioxidative properties and increased cell viability in response to $H_2O_2$-induced oxidative stress than aRPE-PU cells.

2.4 Oct4/SirT1 Gene Transfer Improved Light-Injured Retina

Figure 7:
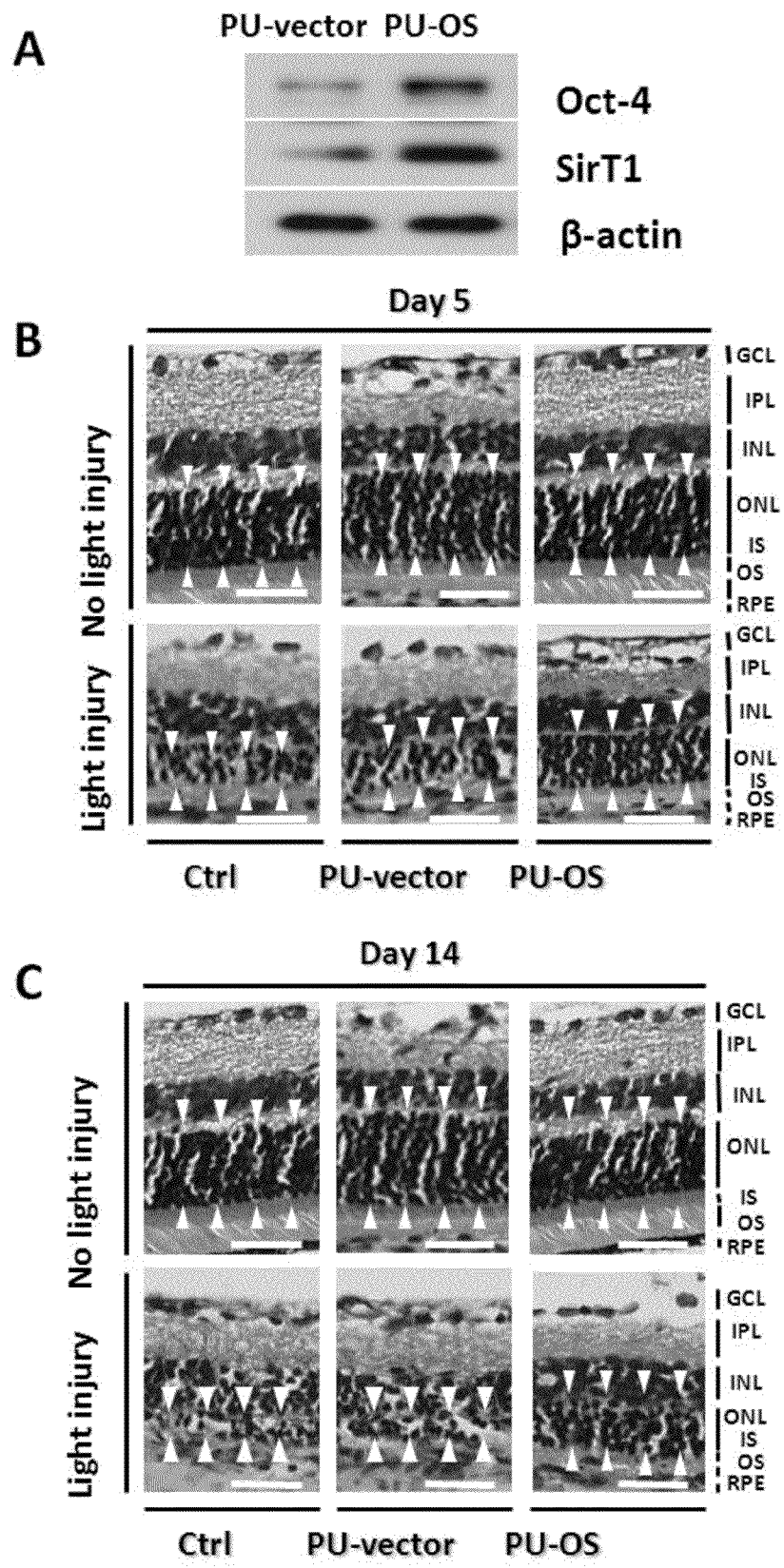
FIG. 7 provides the results of that PU-OS application acquiring cytoprotective effects in light-injured retina, wherein (A) shows the western blot analysis of Oct4 and SirT1 expression in retinal tissues after injection of either PU-OS or PU-vector; (B)-(C) show the representative images of H&E staining for retinal sections at day 5 (B) and day 14 (C) after intense light injury; (D)-(E) show the quantification of ONL thickness in the indicated groups (arrowheads in (B) and (C)) at day 5 (D) and day 14 (E), respectively, after intense light injury; and (F)-(G) show the quantification by immunofluorescence analysis of Oct4-positive and SirT1-positive cells in retinal sections at day 5 and day 14 after light injury (#$p<0.05$; *$p<0.05$; **$p<0.01$; Bar=40 µm; data shown are the mean±SD of three independent experiments; GCL, ganglion cell layer; IPL, inner plexiform layer; INL, inner nuclear layer; ONL, outer nuclear layer; IS, inner segment; OS, outer segment; RPE, retinal pigment epithelium).
Figure 7:
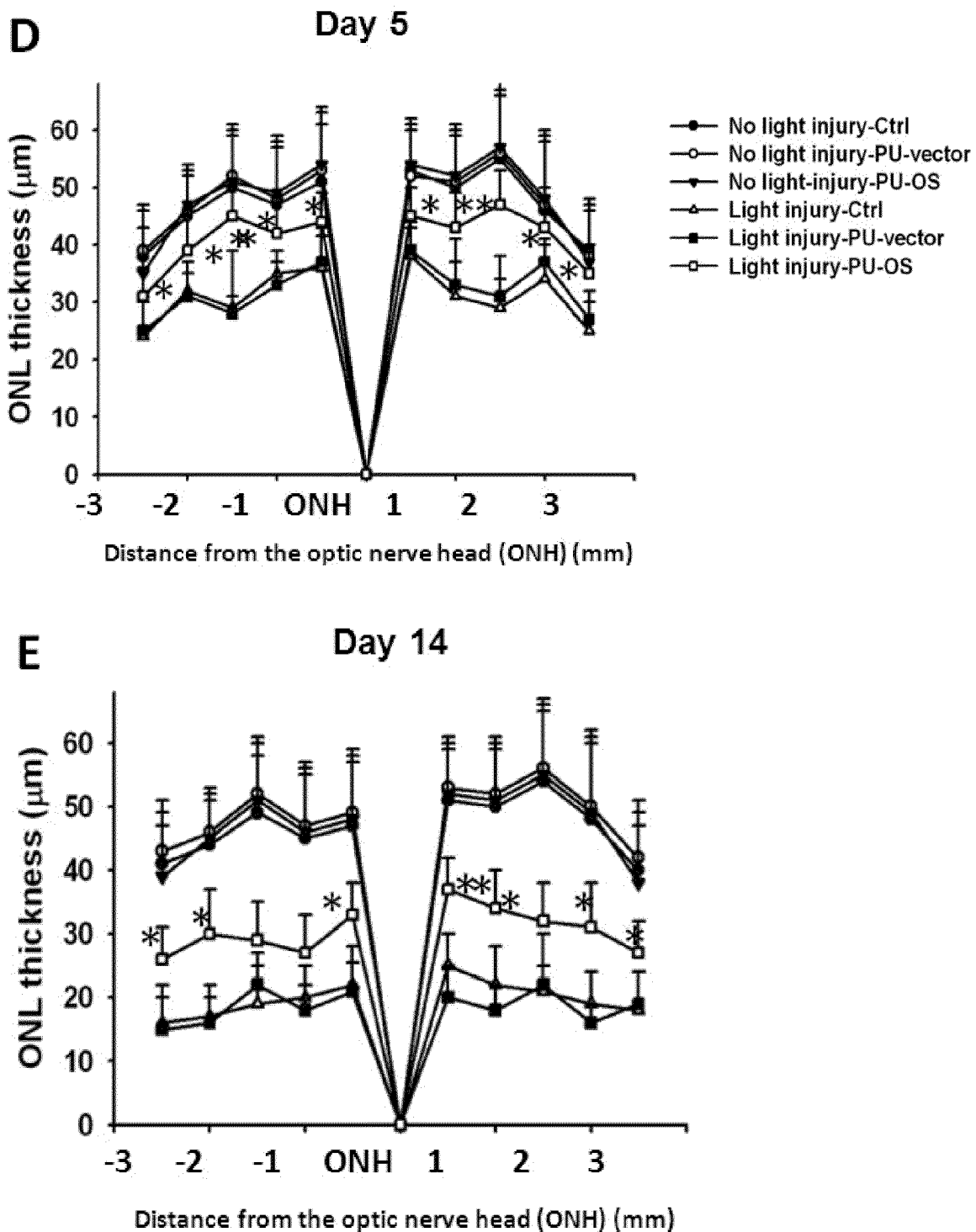
Figure 7:
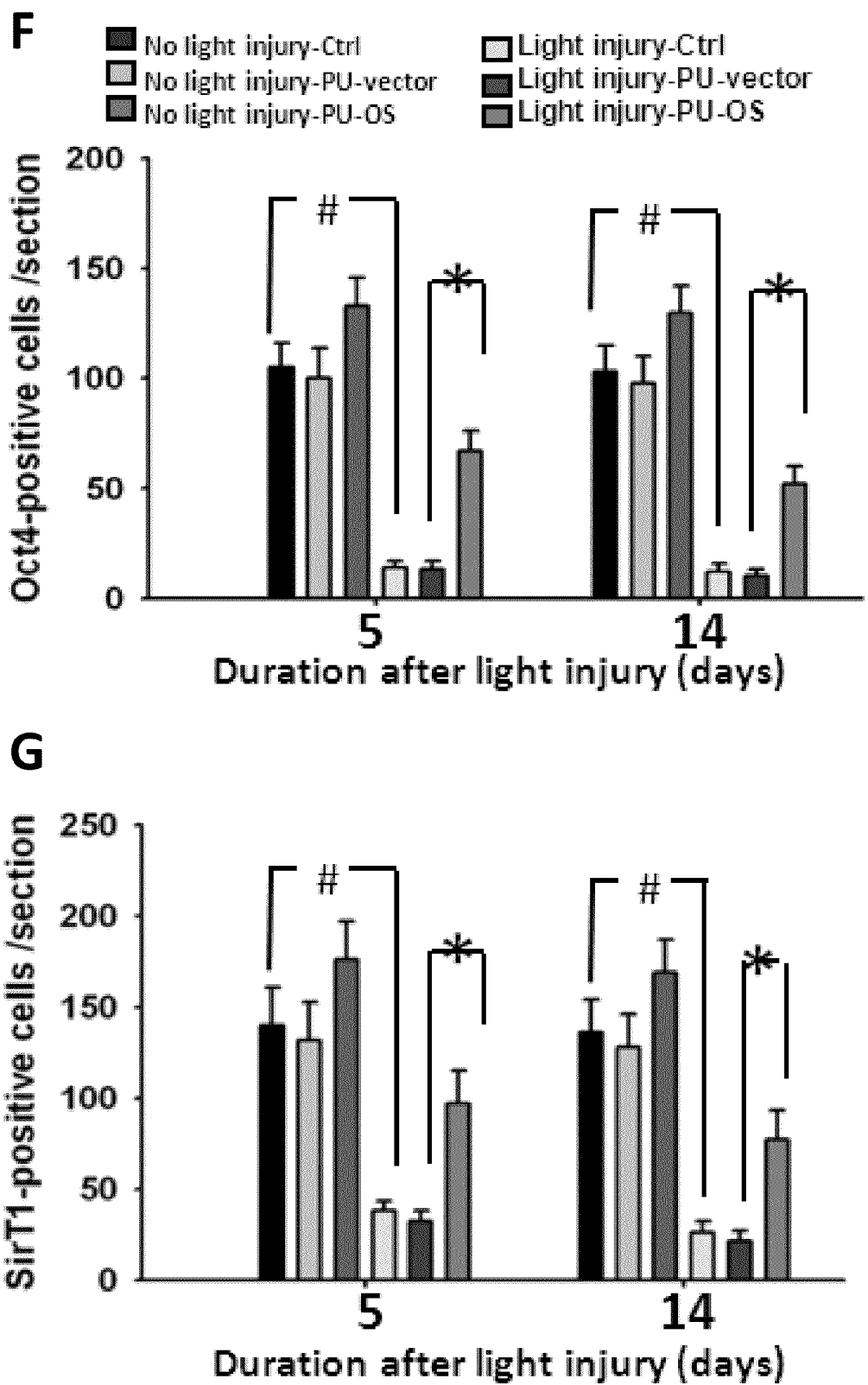

To examine if PU vectors can efficiently transduce Oct4/SirT1 into retinal tissue, the expression of these two proteins was evaluated in homogenized retina two weeks after gene delivery (FIG. 7A). Western blot analysis showed significantly increased Oct4 and SirT1 protein levels in PU-administered retinal tissue, indicating successful exogenous transduction of the two genes by subretinal injection of PU-OS. To evaluate the rescuing effect of Oct4/SirT1 gene delivery on light-injured rat retinas, the change in the outer nuclear layer (ONL) thickness was examined at 5 days and 2 weeks (FIGS. 7B and 7C) after light exposure. In the control and PU-vector-treated rats, light exposure significantly reduced ONL thickness compared to the rats receiving no light exposure (FIGS. 7B and 7C). The application of PU-OS to the light-exposed rats significantly suppressed ONL thinning compared to PU-vector-treated light-exposed animals (FIGS. 7B and 7C). Based upon these data, the protective effect of PU-OS application on light-induced ONL thinning could be maintained until 2 weeks. Compared to the average ONL thickness after PU vector treatment at 5 days (34.3±5.6 µm) and 2 weeks (19.9±3.1 µm) after light exposure, PU-OS treatment significantly suppressed the light-induced ONL thinning at 5 days (43.5±6.1 m) and 2 weeks (31.7±4.2 µm), respectively (both p<0.05, FIGS. 7D and 7E). To further determine the expression of Oct4 and SirT1 protein after PU-OS application in light-injured rat retinas, a triple-staining immunofluorescence assay was used. Oct4 and rhodopsin (photoreceptor marker) signals were detected in the light-injured retina (blue, DAPI: nuclei staining) at Day 3 after light exposure. As a result, prominent Oct4 immunoreactivity in the ONL of the PU-OS-treated retina was found as compared with the PU-vector-treated retina. The percentage of Oct4-positive cells at Day 5 in 14 light-injured retinas was significantly higher in the retina with PU-OS treatment than in retina treated with the PU vector (p<0.05; FIG. 7F). The percentage of SirT1-positive cells (FIG. 7G) in the light-injured PU-OS-treated retinas were also higher as compared to the PU vector-treated retinas. These findings indicated cytoprotective effects in light-injured rat retinas following PU-mediated delivery of the Oct4 and SirT1 genes.

2.5 Oct4/SirT1 Delivery Recovered Impaired ERG

Figure 8:
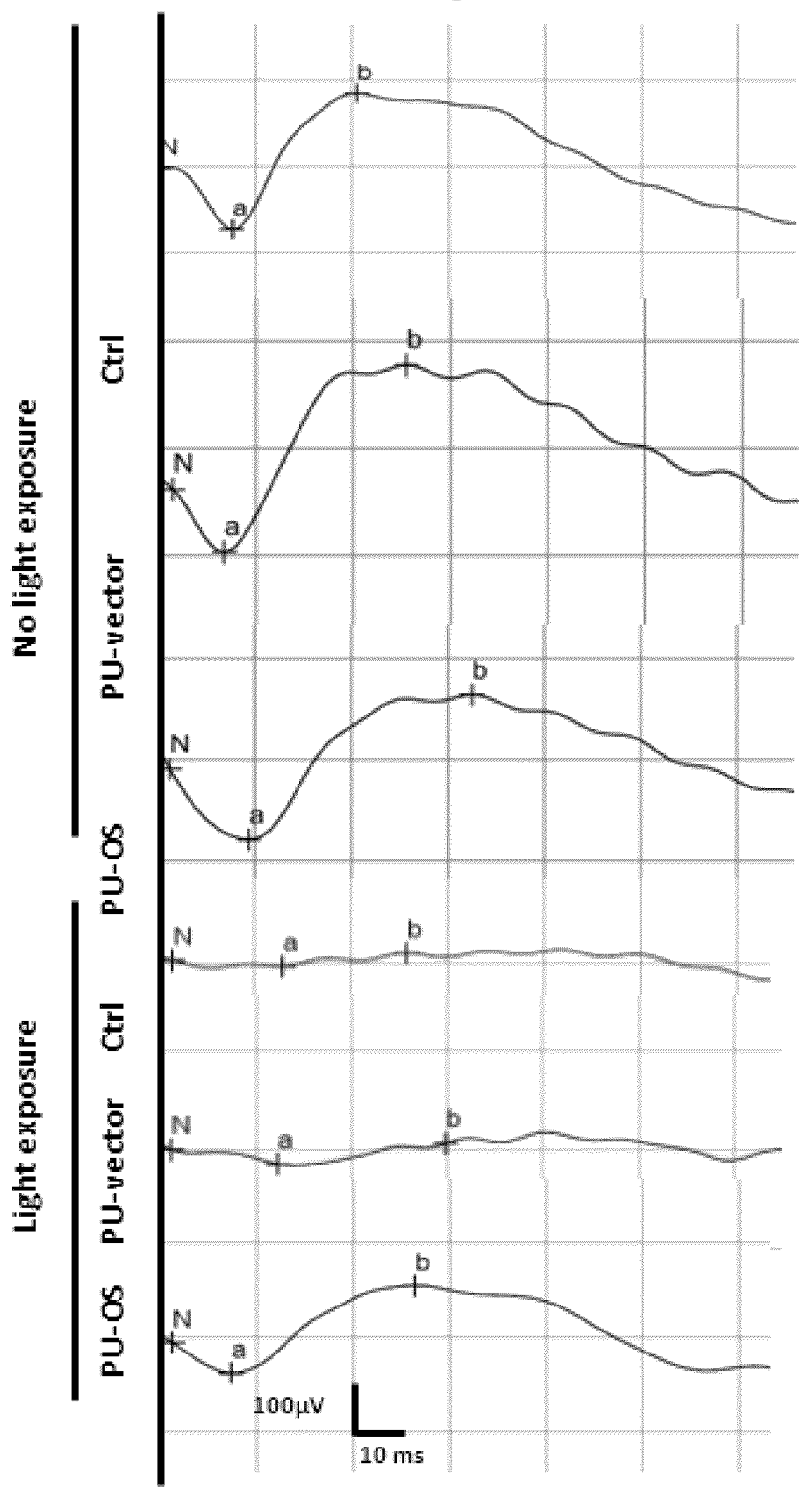
FIG. 8 provides the results of PU-OS treatment recovering retinographic responses and enhancing antioxidant levels in light-injured retina, wherein (A)-(B) show the representative ERG wave responses at day 5 (A) and day 14 (B) after intense light injury; (C)-(D) show the quantification of a-wave (C) and b-wave (D) amplitudes at day 5 and day 14 after light injury; (E)-(H) show the relative changes in the MDA level (E), and SOD (F), CAT(G), and GSH-Px (H) activities at day 5 after light injury (#$p<0.05$; *$p<0.05$; data shown are the mean±SD of three independent experiments); and (I) shows the qRT-PCR results quantifying relative amounts of PGC-1α mRNA in indicated groups at day 5 after light injury.
Figure 8:
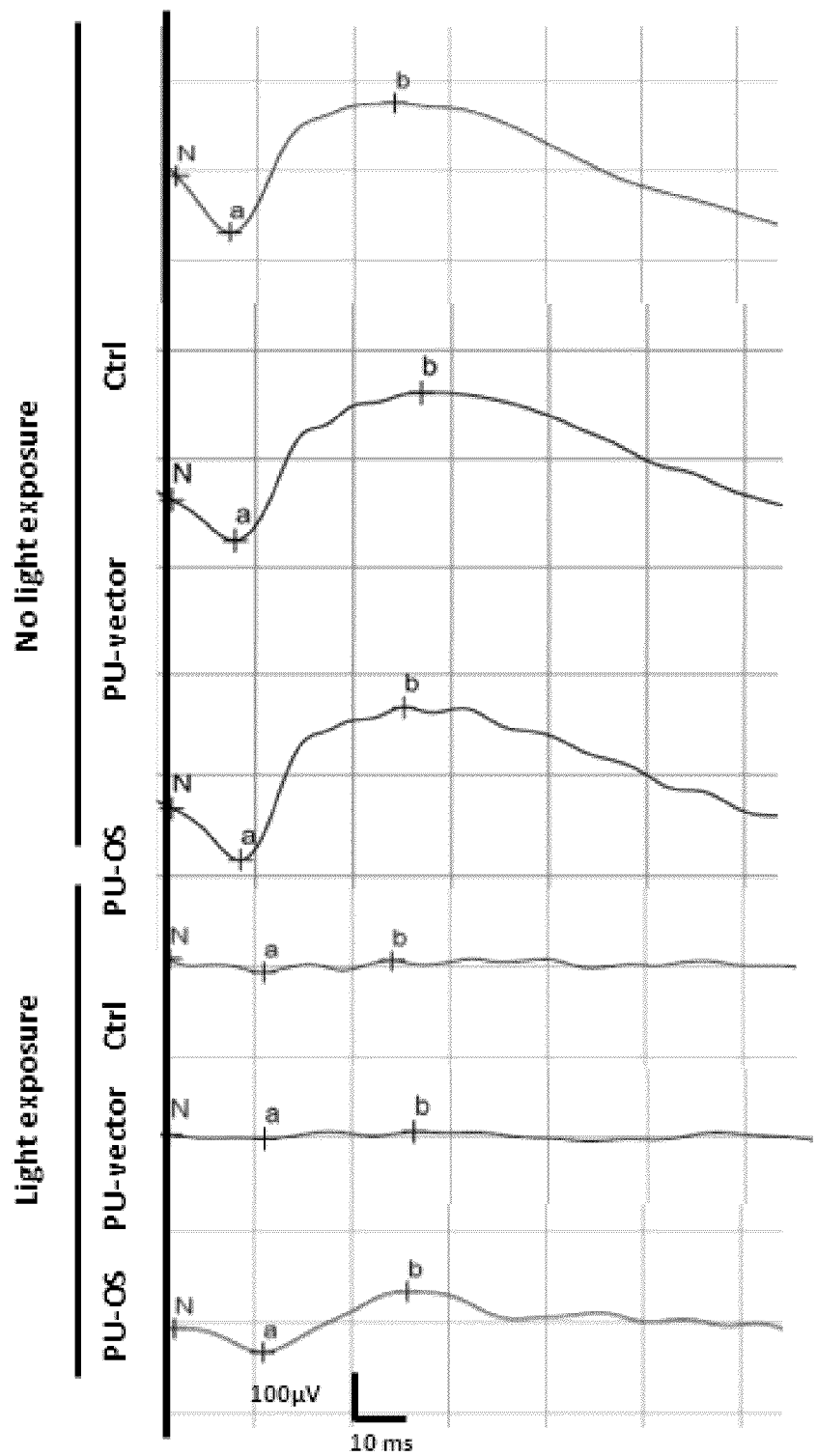
Figure 8:
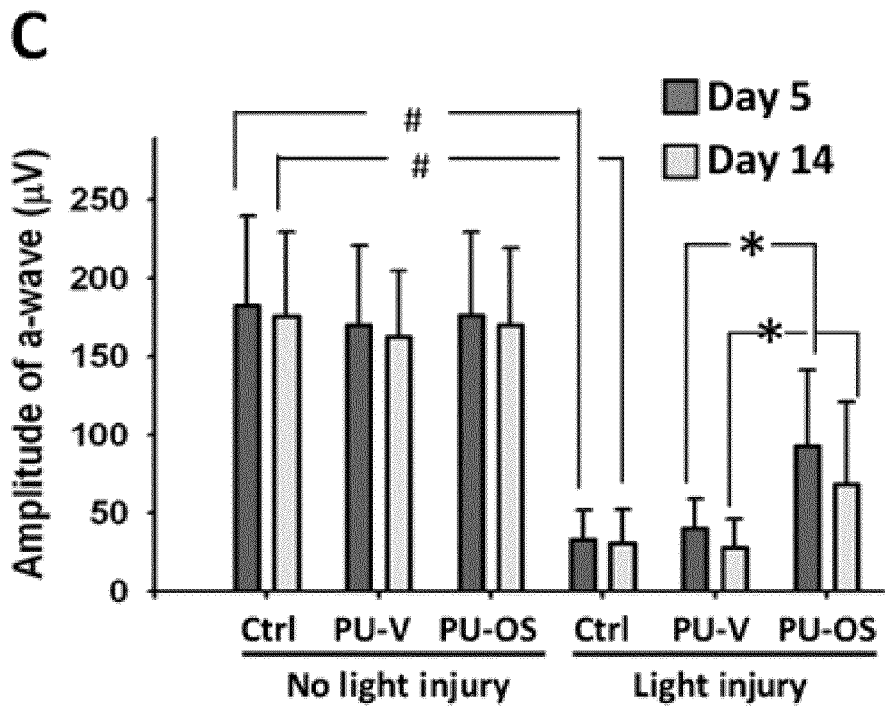
Figure 8:
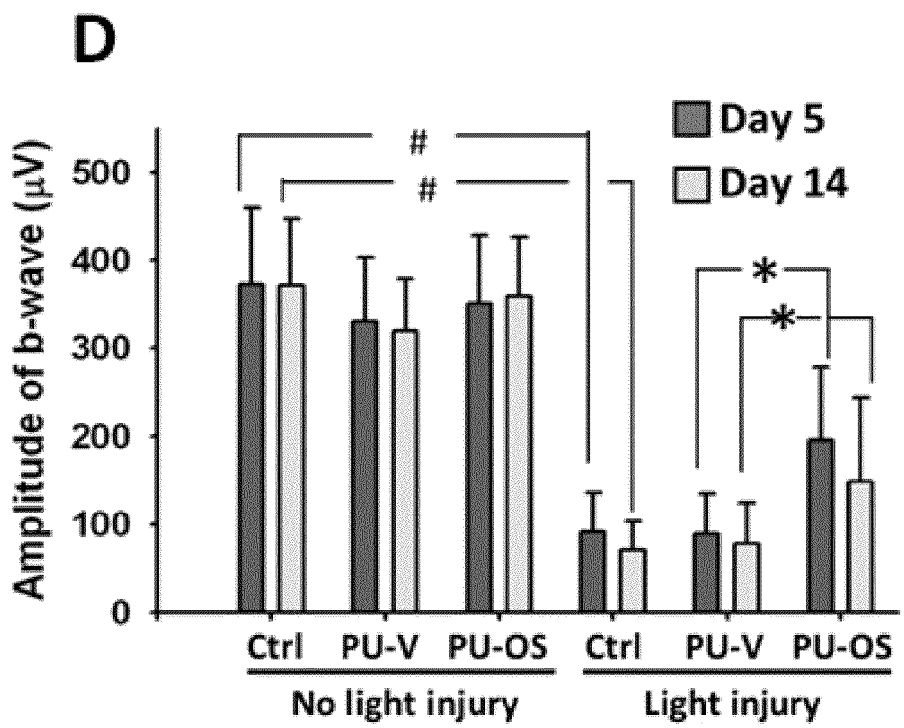
Figure 8:
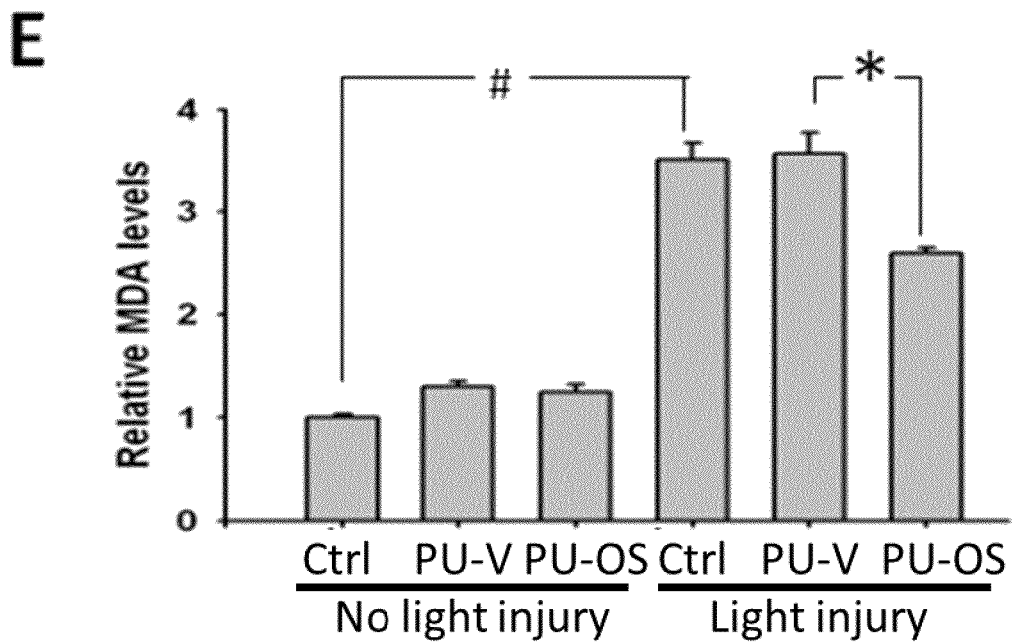
Figure 8:
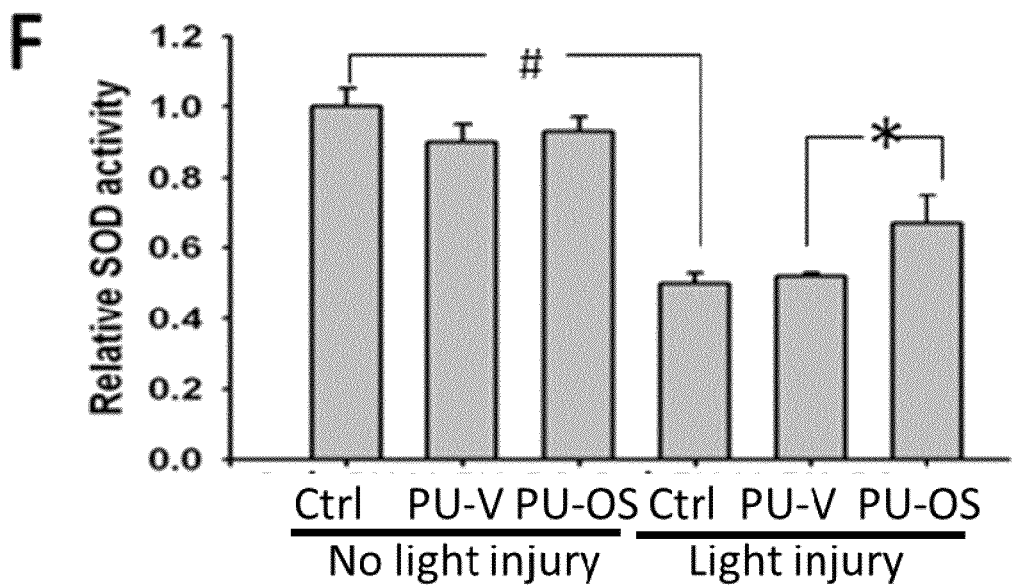
Figure 8:
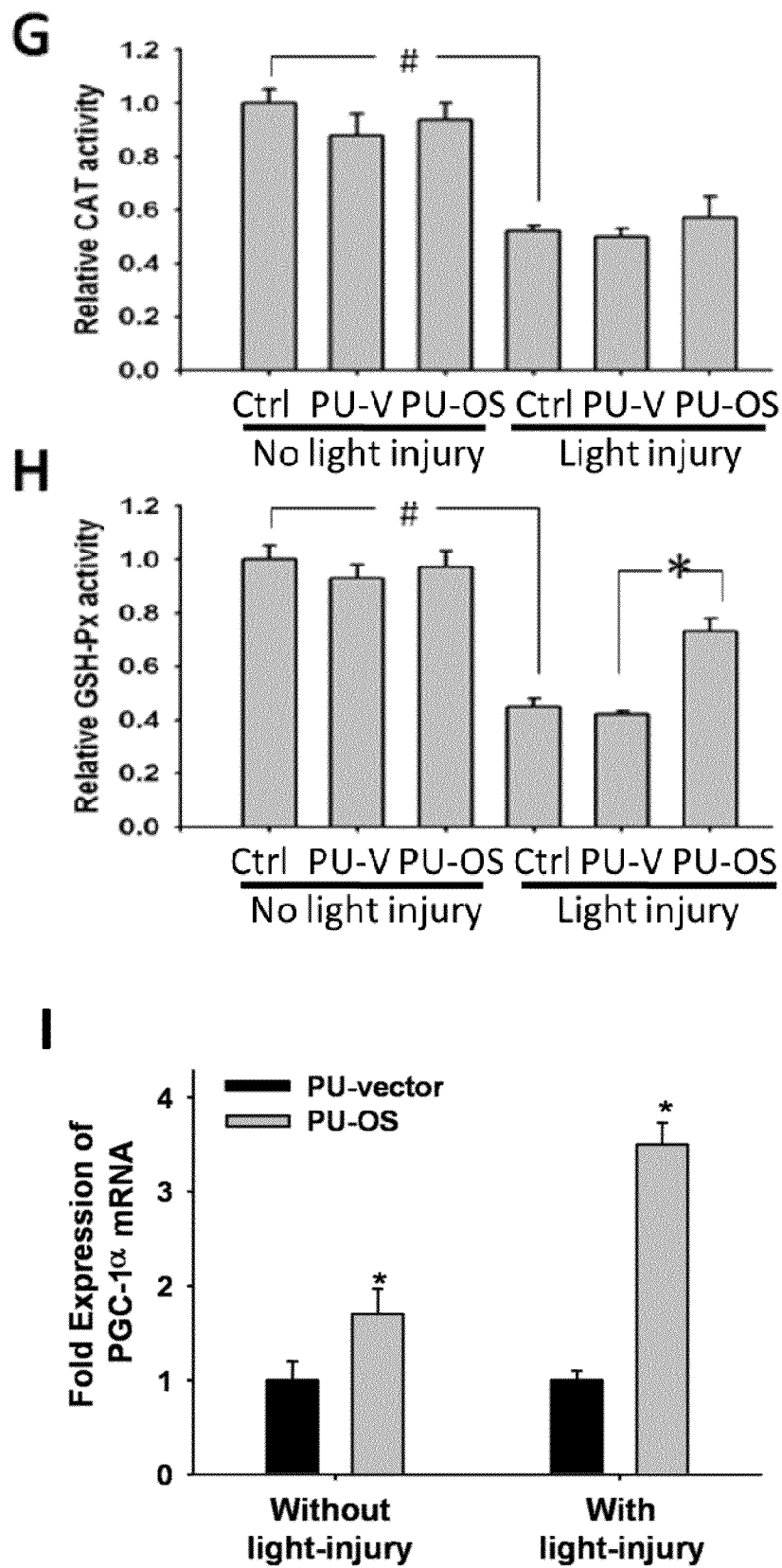

To investigate the effect of PU-OS application on light-induced retinal dysfunction, changes in the ERG response were observed at 5 days and 2 weeks after light exposure (FIGS. 8A and 8B). In control rats, light exposure led to a significant reduction in the average a-wave and b-wave amplitudes at Day 5 (35.7±17.4 µV and 91.7±39.4 µV, respectively; FIGS. 8C and 8D) compared to control rats receiving no light exposure (179.2±61.3 µV and 387.5±71.8 µV for average a-wave and b-wave amplitudes, respectively; FIGS. 8C and 8D). The application of PU-OS to light-exposed rats at Day 5 significantly minimized the reduction of the average a-wave (95.3±45.8 µV) and b-wave (197.2±78.4 µV) amplitudes (both p<0.05, FIGS. 8C and 8D) as compared to those of the PU vector treatment in light-exposed animals (41.2±17.2 µV and 88.2±46.4 µV for average a-wave and b-wave amplitudes, respectively).

A similar reduction in the average a-wave (32.9±18.2 µV) and b-wave (71.4±31.5 µV) amplitudes (both p<0.05, FIGS. 8C and 8D) was observed at 2 weeks in control rats with light exposure as compared to control rats receiving no light exposure (174.6±45.6 µV and 376.6±67.5 µV for the average a-wave and b-wave amplitudes, respectively). At this time point, PU-OS application to light-exposed rats significantly minimized the reduction in the average a-wave (67.2±45.2 µV) and b-wave (147.3±85.2 µV) amplitudes (both p<0.05, FIGS. 8C and 8D) as compared to that for the PU vector treatment in light-exposed animals (28.2±15.8 µV and 77.8±47.2 µV for the average a-wave and b-wave amplitudes, respectively). Our data demonstrate that the delivery of PU-OS suppressed light injury-induced reduction in retinal ERG a- and b-wave amplitudes.

Because our findings demonstrate a significant antioxidation effect for Oct4 and SirT1 co-overexpression in aRPE-PU-OS cells (FIG. 6), we further evaluated the levels of retinal MDA and the activity of antioxidant enzymes (SOD, CAT and GSH-Px) in PU-OS or PU vector-treated rats at Day 5 after light exposure. Light exposure increased MDA levels (FIG. 8E) and suppressed the activity of the antioxidant enzymes (FIG. 8F-H). Importantly, PU-OS treatment in light-injured retina resulted in lower MDA levels (FIG. 8E), increased PGC-1α levels (FIG. 8I), and higher SOD and GSH-Px activities but not CAT activity (FIG. 8F-H) compared to the PU vector treatment. These data indicated that OS overexpression in light-injured rat retinas provides resistance to oxidative stress-related damage and further facilitated retinal function recovery.

We claim:

1. A method for decreasing the level of methylation of octamer-binding transcription factor 4 (Oct4) promoter in a target mammalian cell, comprising transfecting the target mammalian cell with a plasmid comprising Oct4 cDNA and a plasmid comprising sirtuin 1 (SirT1) cDNA, wherein the Oct4 cDNA and the SirT1 cDNA transfected are in a quantity being effective in a synergistic manner in decreasing the level of methylation of endogenous Oct4 gene promoter.

2. The method of claim 1, wherein the Oct4 cDNA comprises the nucleic acid sequence of SEQ ID NO: 1.

3. The method of claim 1, wherein the SirT1 cDNA comprises the nucleic acid sequence of SEQ ID NO: 2.

4. The method of claim 1, wherein the plasmids are delivered by a polymer.

5. The method of claim 4, wherein the polymer is cationic polyurethane-short branch polyethylenimine (PU-sbPEI).

6. The method of claim 1, wherein the plasmid comprising Oct4 cDNA and the plasmid comprising SirT1 cDNA are in a ratio between 0.8:1 and 1:1.2.

7. The method of claim 6, wherein the plasmid comprising Oct4 cDNA and the plasmid comprising SirT1 cDNA are in a ratio of 1:1.

8. The method of claim 1, wherein the target mammalian cell is a retinal pigment epithelium cell.

* * * * *